United States Patent
Fathman et al.

(10) Patent No.: US 11,701,406 B2
(45) Date of Patent: Jul. 18, 2023

(54) COMBINATION OF LOW DOSE IL-2 AND AN INHIBITOR OF TREG IL-2R DESENSITIZATION TO TREAT AUTOIMMUNE AND ALLERGIC INFLAMMATORY DISEASES

(71) Applicant: The Board of Trustees of the Leland Stanford Junior University, Stanford, CA (US)

(72) Inventors: C. Garrison Fathman, Stanford, CA (US); Luis R. Soares, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 514 days.

(21) Appl. No.: 16/614,626

(22) PCT Filed: May 25, 2018

(86) PCT No.: PCT/US2018/034591
§ 371 (c)(1),
(2) Date: Nov. 18, 2019

(87) PCT Pub. No.: WO2018/218119
PCT Pub. Date: Nov. 29, 2018

(65) Prior Publication Data
US 2021/0379155 A1 Dec. 9, 2021

Related U.S. Application Data

(60) Provisional application No. 62/511,002, filed on May 25, 2017.

(51) Int. Cl.
| | | |
|---|---|---|
| A61K 38/20 | (2006.01) |
| A61P 37/06 | (2006.01) |
| A61P 3/10 | (2006.01) |
| A61K 31/352 | (2006.01) |
| A61K 31/428 | (2006.01) |
| A61K 31/4365 | (2006.01) |
| A61K 31/4468 | (2006.01) |
| A61K 31/451 | (2006.01) |
| A61K 31/496 | (2006.01) |
| A61K 31/498 | (2006.01) |
| A61K 31/519 | (2006.01) |
| A61K 31/538 | (2006.01) |
| A61K 31/7064 | (2006.01) |
| A61K 31/7076 | (2006.01) |

(52) U.S. Cl.
CPC ........ *A61K 38/2013* (2013.01); *A61K 31/352* (2013.01); *A61K 31/428* (2013.01); *A61K 31/4365* (2013.01); *A61K 31/4468* (2013.01); *A61K 31/451* (2013.01); *A61K 31/496* (2013.01); *A61K 31/498* (2013.01); *A61K 31/519* (2013.01); *A61K 31/538* (2013.01); *A61K 31/7064* (2013.01); *A61K 31/7076* (2013.01); *A61P 3/10* (2018.01); *A61P 37/06* (2018.01)

(58) Field of Classification Search
None
See application file for complete search history.

(56) References Cited

U.S. PATENT DOCUMENTS

| | | | | |
|---|---|---|---|---|
| 4,748,234 A | * | 5/1988 | Dorin | C07K 1/1133 530/424 |
| 2021/0252160 A1 | * | 8/2021 | Soares | A61P 37/02 |

FOREIGN PATENT DOCUMENTS

WO 2013067396 A2 5/2013

OTHER PUBLICATIONS

Katre et al., "Chemical modification of recombinant interleukin 2 by polyethylene glycol increases its potency in the murine Meth A sarcoma model", 1987, Proc . Natl. Acad. Sci., 84(6), pp. 1487-1491. (https://doi.org/10.1073/pnas.84.6.1487) (Year: 1987).*

* cited by examiner

Primary Examiner — My-Chau T. Tran
(74) Attorney, Agent, or Firm — Pamela J. Sherwood; Bozicevic, Field & Francis LLP

(57) ABSTRACT

Provided herein are methods and compositions for treating inflammatory disease by the administration, to a patient in need thereof, of an inhibitor of IL-2R desensitization in combination with a low dose of IL-2. A low dose of interleukin-2 (IL-2) is sufficient to stimulate regulatory T lymphocytes (Tregs) without substantially inducing effector T lymphocytes (Teffs). In some embodiments, the inhibitor of IL-2R desensitization is a small molecule or drug. Is some embodiments the inhibitor is a NEDD8 activating enzyme (NAE) inhibitor. In some embodiments a combination therapy provides for a synergistic effect, where the combination of the inhibitor of IL-2R desensitization and low dose IL-2 provides an effect that is greater than the sum of either the inhibitor or low dose IL-2 administered as a single agent.

14 Claims, 5 Drawing Sheets

Tregs from SLE patients are deficient in GRAIL

COMBINATION OF LOW DOSE IL-2 AND AN INHIBITOR OF TREG IL-2R DESENSITIZATION TO TREAT AUTOIMMUNE AND ALLERGIC INFLAMMATORY DISEASES

CROSS-REFERENCE TO RELATED APPLICATIONS

This application claims the benefit of U.S. Provisional Application No. 62/511,002, filed May 25, 2017, the disclosure of which is incorporated herein by reference.

BACKGROUND

The present invention relates to novel therapies for treating autoimmune and allergic "inflammatory" diseases. More specifically, the present invention relates to a combination of low dose interleukin-2 and an inhibitor of IL-2R desensitization, including, for example, small molecule inhibitors of neddylation of cullin5 which may include without limitation NEDD8 activating enzyme (NAE) inhibitors, for the treatment of systemic lupus erythematosus, (SLE) type one diabetes (T1D), multiple sclerosis (MS), severe allergy, and other autoimmune and inflammatory diseases, including graft versus host disease (GVHD).

Antigenic stimulation of naïve T cells results in activation and/or differentiation of effector (Teff) and regulatory (Treg) cells, or alternatively, can result in anergy or apoptosis. In order to achieve this initial activation, a number of coordinate signals are required, including activation of the T cell receptor (TCR) together with a second set of signals delivered by costimulatory receptors. Co-receptors include CD28, cytotoxic T lymphocyte antigen 4 (CTLA4), inducible T cell co-stimulator (ICOS), and programmed cell death protein 1 (PD-1) and CD7, and can function as co-stimulators (CD28, ICOS and CD7) or co-repressors (CTLA4, PD-1) of T cell activation. The scientific literature reflects a long debate on the question whether the TCR and the co-receptors induce separate signal pathways or whether the signaling routes employed by both receptor systems are entirely overlapping.

One of the consequences of activating CD4 T cells is triggering their secretion of cytokines that signal a variety of cell types including CD4 T cells through engaging the relevant cytokine receptor. One cytokine, interleukin 2 (IL-2) is essential in a variety of activation schema. Important for the purposes of this application is the ability of IL-2 to signal regulatory CD4 T cells that constitutively express the high affinity IL-2 receptor (IL-2R), to both activate and drive their proliferation and function. IL-2 binds to the IL-2 receptor, which has three forms, generated by different combinations of three different proteins, often referred to as "chains": α (alpha) (also called IL-2Rα, CD25, or Tac antigen), β (beta) (also called IL-2Rβ, or CD122), and γ (gamma) (also called IL-2Rγ, $\gamma_c$, common gamma chain, or CD132); these subunits are also parts of receptors for other cytokines. The α chain (CD-25), along with the beta and gamma chain, the high affinity IL-2 receptor, is constitutively expressed on regulatory CD4 T cells but is absent on resting CD4 T cells of other types. The α chain binds IL-2 with low affinity; the combination of β and γ together form a complex that binds IL-2 with intermediate affinity, primarily on resting CD4 T cells, memory T cells and NK cells; and all three receptor chains form a complex that binds IL-2 with high affinity (Kd~10-11 M) on activated T cells and regulatory T cells. The three IL-2 receptor chains span the cell membrane and extend into the cell, thereby delivering biochemical signals to the cell interior when IL-2 binds the IL-2R. The α chain does not participate in signaling, but the β chain is complexed with an enzyme called Janus kinase 1 (JAK1), that is capable of adding phosphate groups to molecules including members of the signal transducer and activator of transcription (Stat) family members.

The JAK-STAT system consists of three main components: (1) a receptor (2) Janus kinase 1 (JAK1) and (3) Signal Transducer and Activator of Transcription 5 (STAT5). The IL-2R is activated by IL-2 which in turn activates the kinase function of JAK1, which autophosphorylates itself (phosphate groups act as "on" and "off" switches on proteins). The STAT5 protein then binds to the phosphorylated receptor, where STAT5 is phosphorylated by pJAK1. The phosphorylated STAT5 protein binds to another phosphorylated STAT5 protein (dimerizes) and translocates into the cell nucleus. In the nucleus, it binds to DNA and promotes transcription of genes responsive to STAT5. In response to IL-2 engagement of IL-2R, two STAT5 family members are phosphorylated by the receptor-associated kinase JAK1, STAT5a and STAT5b, and then form homo- or heterodimers that translocate to the cell nucleus where they act as transcription activators.

Some clues to maintenance of the T cell resting state have been found in members of the E3 ubiquitin ligase family, which have been demonstrated to be important molecular mediators of T cell anergy and peripheral tolerance. The ubiquitination process requires the E1 enzyme to activate ubiquitin, an E2 enzyme to act as a transferase, and an E3 ligase to direct substrate specificity for ubiquitination. The E3 ubiquitin ligases Cbl-b, Itch, and gene related to anergy in lymphocyte (GRAIL) have all been described as playing a functional role in T cell anergy. Although GRAIL was first detected during the induction of anergy in CD4 T cell clones, recent studies have demonstrated that it plays a central role in Treg function, as GRAIL knock out mice have diminished Treg function and transfection of conventional CD4 T cells with a construct for GRAIL expression turns the conventional CD4 T cells into regulatory cells.

Regulatory T cells are T lymphocytes having immunosuppressive activity. Natural Tregs are characterized as $CD4^+CD25^+Foxp3^+$ cells. A Treg quantitative or qualitative defect has been described in many human autoimmune diseases, including systemic lupus erythematosis (SLE), Type 1 Diabetes (T1D), Multiple Sclerosis (MS), inflammatory bowel disease (IBD), uveitis and myositis as well as other prototypic autoimmune diseases and in human allergic diseases. Conversely, addition of or restoration of Treg function induces clinical improvements in most animal models of these diseases. In SLE, normal immunologic homeostasis is disrupted, with the balance strongly weighted towards sustained T-cell reactivity. The two principal external mechanisms that control T-cell reactivity, Treg suppression and activation-induced apoptosis, have failed. Other manifestations of disrupted immunologic homeostasis in active SLE include impaired host defense. This abnormality may be the secondary sequelae of failed attempts to control self-reactive cells. Finally, lymphocyte production of IL-2 is decreased in SLE.

Applicants have found that the Treg IL-2R responds differently to IL-2 engagement than does the IL-2R of conventional T cell, even the activated CD4 T cell bearing the high affinity receptor, due to the constitutive expression of GRAIL in CD4 Tregs (but not in conventional CD4 T cells). Treg associated GRAIL ubiquitinates a member of the suppressor of cytokine signaling (SOCS3) cullin ring ligase (CRL) multiprotein ubiquitin ligase complex, cullin5. That ubiquitination competes with a different requisite post translational modification (neddylation) of cullin5 at the exact lysine that is ubiquitinated by GRAIL. Neddylation (a post translational modification that is similar to ubiquitination, but attaches NEDD8 instead of ubiquitin) of cullin lysine is required to allow the SOCS CRL to ubiquitinate and thus degrade pJAK1 associated with the IL-2R, to turn off the IL-2R signaling, called receptor desensitization. Neddylation allows the RBX1 (ring box protein) tethered at one end of cullin5 and bound to the E2 ubiquitin transferase of the CRL, to be partially released, bringing the E2 that transfers ubiquitin to the substrate bound by SOCS3 (the E3 in this instance) bound to the RBX in proximity of the substrate pJAK1 (a 50 angstrom change in position of the E2 made possible by the partial release of one end of the bound RBX).

In model systems, it is well established that low dose IL-2 promotes selective expansion of regulatory T cells (Treg), an IL-2 responsive cell type known to control autoimmunity. Moreover, many autoimmune diseases are marked by defects in Treg and/or IL-2/IL-2 receptor signaling. Thus, patients with immune-mediated diseases have been treated with low dose IL-2 with the goal of increasing Tregs and controlling autoimmunity. In graft versus host disease, HCV-induced vasculitis, SLE, and type 1 diabetes (T1D), Treg numbers increased with low dose IL-2 therapy.

These studies on the use of low dose IL-2 to treat inflammatory diseases include chronic GVHD (Koreth et al. (2011) N Engl J Med. 365(22):2055-66; Kennedy-Nasser et al. (2014) Clin Cancer Res. 20(8):2215-25; Matsuoka et al. (2013) J. Sci Transl Med. 2013 5(179):179ra43), HCV induced vasculitis (Saadoun et al. (2011) N Engl J Med. 365(22):2067-77; Oo et al. (2012) N Engl J Med. 366(14): 1353-4), SLE (He et al. (2016) Nature Med 22(9):991-3), and type one diabetes (Hartemann et al. (2013) Lancet 1(4):295-305.

The initial use of low dose IL-2 in therapy of these diseases was based on the assumption that IL-2 would facilitate regulatory T cell (Treg) growth survival and function due to the presence of the high affinity IL-2 receptor on Tregs, and thus prove beneficial in therapy of inflammatory diseases in which there was a deficiency in number and/or function of Tregs. However, there has been a lack of long term efficacy for low dose IL-2 administered as a single agent; and a number of individuals that are unresponsive to low dose IL-2 administered as a single agent.

SUMMARY

Provided herein are improved methods for treatment of autoimmune and inflammatory diseases, by administering to a subject a NEDD8 activating enzyme (NAE) inhibitor (an inhibitor of Treg IL-2R desensitization) and a low dose of IL-2. In some embodiments, the administration of IL-2 expands the number of Tregs in the subject, and the inhibitor of neddylation increases/restores the function of the Tregs by delaying IL-2R desensitization.

Compositions and methods are provided for the treatment of inflammatory autoimmune diseases, including without limitation, SLE, RA, T1D, IBD, MS, psoriasis and other autoimmune diseases as well as serious allergic disease by the administration to a patient in need thereof of an inhibitor of IL-2R desensitization (such as an NAE inhibitor) and a low dose of IL-2. A low dose of interleukin-2 (IL-2) is that dose which is sufficient to expand regulatory T lymphocytes (Tregs), without substantially activating effector T lymphocytes (Teffs). In some embodiments the inhibitor of IL-2R desensitization is an inhibitor of neddylation. In some embodiments the inhibitor is a NEDD8-activating enzyme inhibitor (NAE inhibitor).

In some embodiments, an NAE inhibitor is administered to a subject in need thereof in a combination therapy with a low dose of IL-2, which combination of low dose IL-2 and NAE inhibitor provides for a synergistic effect, where the combination of NAE inhibitor and low dose IL-2 provides an effect that is greater than the sum of either the NAE inhibitor or low dose IL-2 administered as a single agent. A benefit of the present invention can be the use of lowered doses of the agents relative to the dose required as a single agent. A benefit of the present invention can also, or alternatively, be a decrease in the length of time required for treatment or the length of time required for initial response to treatment, relative to the length of time required for treatment as a single agent. A benefit of the present invention can also, or alternatively, be an enhanced response relative to the response observed after treatment with a single agent.

In some embodiments of the invention, the inflammatory disease is SLE. Without being limited by the theory, applicants have made the unexpected observation that GRAIL expression, which is important in Treg function, is markedly diminished in Treg cells from SLE patients with active disease, which individuals were observed to have diminished Treg function. These SLE Treg cells further had a defect in the normal inhibition of IL-2R desensitization. Neddylation is required for SOCS3-Elongin-Cullin5 E3-ligase activity, thus ubiquitination of Lys 724 on Cullin5 (in mice) by GRAIL can inhibit the ability of the SOCS-Elongin-Cullin5 E3 complex to ubiquitinate pJAK1, allowing prolonged IL-2R STAT5 signaling in the low dose IL-2 activated Tregs due to inhibition of desensitization of the receptor signaling. Loss of the STAT5b isoform in humans can lead to defective Tregs and the development of autoimmune diseases. By GRAIL's competing for neddylation of Cullin5, the functional activation of Tregs by low dose IL-2 is potentiated. Low dose IL-2 expands the Tregs, inhibition of receptor desensitization increases their function.

In some embodiments, the methods described herein stimulate expansion and/or function of regulatory T lymphocytes (Tregs), without substantially inducing effector T lymphocytes (Teffs) in a human subject. The methods disclosed herein may allow for an increase in the Treg/Teff balance, i.e. the ratio of Treg/Teff is increased. The methods disclosed herein may also increase potency of suppressive Treg cell activity in said subject. The methods and compositions may, in some embodiments, be used for the treatment or prevention of any condition associated with, or caused by, ineffective Treg function. The methods are particularly suited for treating inflammatory, immune-related or autoimmune diseases, including without limitation GVHD, HCV-related vasculitis, uveitis, myositis, type I diabetes, systemic lupus erythematous, systemic vasculitis, psoriasis, allergy, asthma, Crohn's disease, Multiple Sclerosis, Rheumatoid Arthritis, atherosclerosis, and autoimmune thyroid disease, as well as serious allergic diseases.

In one aspect, provided herein is a method for treating an inflammatory autoimmune disease in a subject in need thereof, by administering to the subject an NAE inhibitor in combination with an effective low dose of IL-2. In another aspect, provided herein is the use of a low dose of IL-2, and an NAE inhibitor in the preparation of a medicament for treating a subject with an inflammatory disease. In any of the above aspects, in some embodiments, the subject is administered an NAE inhibitor with a low dose of IL-2, wherein the administration is simultaneous or sequential. In some embodiments, the inflammatory disease is SLE, RA, T1D, IBD, MS, psoriasis, another autoimmune disease, or a serious allergic disease.

In another aspect, provided herein is a kit comprising (i) an NAE inhibitor; and (ii) a low dose of IL-2. In some embodiments, the kit comprises a container and a label affixed to or instructions associated with the container directing administration for treatment. In this and any of the foregoing embodiments, the IL-2 may be in a separate dosage form from the NAE inhibitor. In other embodiments, the IL-2 and NAE inhibitor are admixed or otherwise combined in a single unit dosage form. Various embodiments of such components suitable for use in such kits are described in the examples below and elsewhere herein. Any component in any example may be combined with any other component in any other example below for use in a kit of the invention. Further, any excipient in any amount exemplified in the examples below or described elsewhere herein may be used in any component.

In another aspect, provided herein is a unit dosage form of low dose IL-2 and an NAE inhibitor. In various embodiments, the unit dosage form may, for example, be in solid form, such as, but not limited to, a lyophilized composition; such as a lyophilized composition for reconstitution; a liquid formulation; or packaged with a syringe for delivery. In various embodiments, the unit dosage form is a solid form, but is dissolved in a pharmaceutically acceptable excipient prior to administration to the subject. In various embodiments, the unit dosage form further comprises a pharmaceutically acceptable excipient.

The embodiments herein are equally applicable to all aspects of the invention, including the particular aspects enumerated above.

BRIEF DESCRIPTION OF THE DRAWINGS

FIG. 1A Is a schematic of the low dose IL-2 STAT5 signaling pathway in regulatory T cells. In mouse Tregs, GRAIL ubiquitinates the same lysine (724), that must be neddylated on cullin5 to allow ubiquitin ligase activity of the SOCS3 CRL. By competing for post-translational modification of cullin5, GRAIL inhibits SOCS3 CRL activity and prolongs pJAK1 activity, thus prolonging pSTAT5 transcriptional activity and Treg function. FIG. 1B Depicts kinetics and amplitude of STAT5 phosphorylation (red line) of hTregs (CD25+) vs hTeffs (CD24−) following low dose IL-2 (1 ng/ml) in cultures harvested at the indicated times are significantly increased when compared to conventional CD4 T cells. A western blot of cell extracts from Treg or Teff cells following contacting in vitro with a low dose of IL-2. The blots were stained with an antibody specific for phosphorylated STAT5. It can be seen that there is a prolonged pSTAT5 response by the Treg cells relative to the Teff cells.

TERMS

Figure 1A:
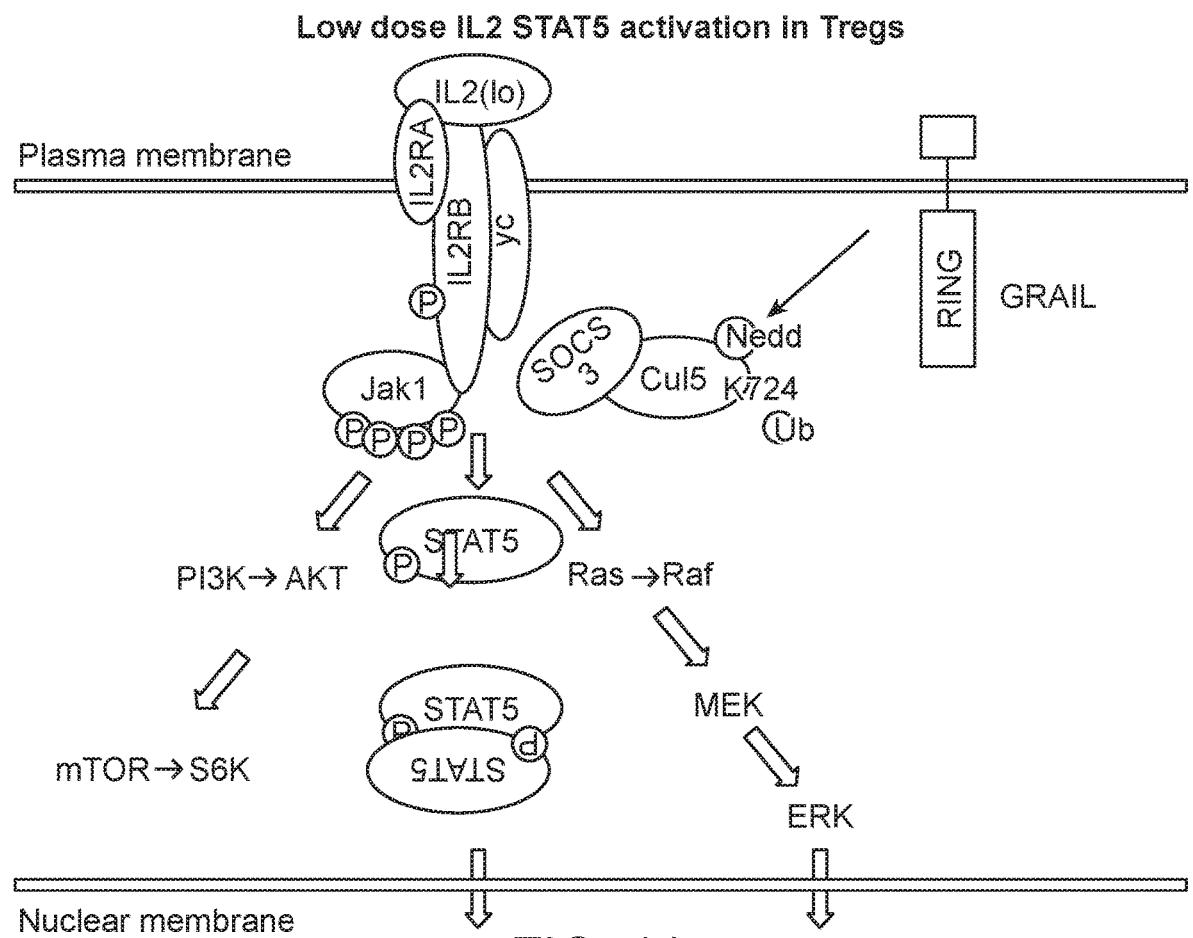
FIGS. 1A-1B.

Administration: As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (including by intratracheal instillation), transdermal, vaginal, or vitreal. In some embodiments, administration may involve intermittent dosing or slow release formulations. In some embodiments, administration may involve continuous dosing (e.g., perfusion) for at least a selected period of time. As is known in the art, IL-2 therapy is commonly administered parenterally (e.g., by intravenous or subcutaneous injection). In some embodiments, the NAE inhibitor, for example, MLN4924, may be administered by infusion.

Inhibitor: As used herein, the term "inhibitor" refers to an agent whose presence or level correlates with decreased level or activity of another molecule. In some embodiments, the inhibitor inhibits IL-2R desensitization, such as inhibition of NEDD8 activating enzyme (NAE). An inhibitor may be or include, for example, a small molecule. An inhibitor may be direct (in which case it exerts its influence directly upon its target) or indirect (in which case it exerts its influence by other than binding to its target; e.g., by interacting with a regulator of the target, so that level or activity of the target is altered).

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheo alveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample.

Biomarker: The term "biomarker" is used herein, consistent with its use in the art, to refer to a to an entity whose presence, level, or form, correlates with a particular biological event or state of interest, so that it is considered to be a "marker" of that event or state. To give but a few examples, in some embodiments, a biomarker may be or comprises a marker for a particular disease state, or for likelihood that a particular disease, disorder or condition may develop. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic or prognostic, of the relevant biological event or state of interest. A biomarker may be an entity of any chemical class. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is found outside of cells (e.g., is secreted or is otherwise generated or present outside of cells, e.g., in a body fluid such as blood, urine, tears, saliva, cerebrospinal fluid, etc.

A specific biomarker of interest relates to the loss of inhibition of the subject's Treg IL-2R following activation by low dose IL-2 in vitro, which can be identified by a more rapid loss of pSTAT5 expression over time compared to a control healthy subject's cells. A suitable biomarker for this effect includes phosphorylated STAT5, which can be detected, for example, by determining binding to an antibody specific for phosphorylated STAT5, e.g. in an ELISA, western blot, flow cytometry, etc.

The term "inflammatory" response is the development of a humoral (antibody mediated) and/or a cellular (mediated by antigen-specific T cells or their secretion products) response. An "immunogen" is capable of inducing an immunological response against itself on administration to a mammal or due to autoimmune disease.

A "subject" or "patient" in the context of the present teachings is generally a mammal. Mammals other than humans can be advantageously used as subjects that represent animal models of inflammation. A subject can be male or female.

Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

In a combination therapy, synergistic combinations may provide for a therapeutic effect that is comparable to the effectiveness of a monotherapy, while reducing adverse side effects, e.g. damage to non-targeted tissues, immune status, and other clinical indicia. Alternatively, synergistic combinations may provide for an improved effectiveness compared to monotherapy, which effectiveness may be measured by diminished signs and symptoms of the autoimmune or inflammatory condition; length of time to relapse; or other indicia of patient health.

Synergistic combinations for combination therapy include the combination of an agent that is targeted to inhibit IL-2R desensitization (such as an NAE inhibitor) and low dose IL-2 treatment. The combination is provided with a combination of agents.

By administration "in parallel," it is meant that the low dose IL-2 and an inhibitor of IL-2R desensitization such an inhibitor of neddylation, are formulated separately and administered separately. In some embodiments, separate administration includes simultaneous administration of the IL-2 and NAE inhibitor as separate dosage forms. In other embodiments, separate administration includes administration of the IL-2 or NAE inhibitor as separate dosage forms administered at different times. In some embodiments of the methods described herein, the low dose IL-2 is administered in parallel with the NAE inhibitor to a subject in need thereof.

By administered "together," it is meant that the low dose IL-2 and the inhibitor of IL-2R desensitization (such as an NAE inhibitor) are formulated in a single pharmaceutical composition. In some embodiments of the methods described herein, the low dose IL-2 is administered together with the NAE inhibitor to a subject in need thereof.

By "effective amount" is meant the amount of a compound required to enhance regulatory $CD4^+$ T cell activity. The effective amount of the low dose IL-2 and the inhibitor of IL-2R desensitization used to practice the present invention for the treatment of an undesirable lack of Treg function may vary depending upon the manner of administration, the age, body weight, and general health of the subject. Ultimately, the attending physician, will decide the appropriate amount and dosage regimen. Such amount is referred to as an "effective" amount.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Dosage Form: As used herein, the term "dosage form" refers to a physically discrete unit of an active agent (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms and schedules.

Dosing Regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen). In some embodiments, administration can be in the form of slow release composition of one or more of the active therapeutic agents.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes autoimmune diseases, serious allergic disease or inflammatory disorders. In some embodiments, the patient is receiving or has received certain therapy to diagnose and/or to treat a disease, disorder, or condition.

Pharmaceutically Acceptable: As used herein, the term "pharmaceutically acceptable" applied to the excipients used to formulate a composition as disclosed herein means that the excipient must be compatible with the other ingredients of the composition and not deleterious to the recipient thereof. Excipients include carriers, diluents, etc.

Pharmaceutical Composition: As used herein, the term "pharmaceutical composition" refers to an active agent, formulated together with one or more pharmaceutically acceptable excipients. In some embodiments, the active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. A pharmaceutical composition may also refer to the combination of two or more agents as described herein for co-administration or administration as part of the same regimen. In some embodiments, a pharmaceutical composition comprises two or more active agents, such as a pharmaceutical composition comprising an NAE inhibitor and IL-2.

Therapeutically Effective Amount: As used herein, the term "therapeutically effective amount" or "therapeutically effective dose" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more signs or symptoms of the disease, disorder, and/or condition.

"Treatment" refers to any administration of a substance that partially or completely alleviates, ameliorates, relives, inhibits, delays onset of, reduces severity of, and/or reduces incidence of one or more symptoms, features, and/or causes of a particular disease, disorder, and/or condition (e.g., SLE, T1D, etc). As with most autoimmune and inflammatory disease therapies, the therapeutic methods described herein are not to be interpreted as, restricted to, or otherwise limited to a "cure"; rather the methods of treatment are directed to the use of the described compositions to "treat", e.g., to effect a desirable or beneficial change in the health of an individual who has the disease in question. Such benefits are recognized by skilled healthcare providers in the field and include, but are not limited to, a stabilization of patient condition, a decrease inflammatory episodes, an improvement in vital functions, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, disease regression in an individual (e.g., as the result of the methods described herein) may also be assessed by taking samples of cells, e.g. blood cells, synovial fluid, etc. and testing the cells for the level of markers to monitor the status of the inflammation, e.g. an increase in functional Treg cells, a prolongation or diminution of pSTAT5 expression in Tregs, a decrease in antibodies directed at autoantigens, etc. Those of ordinary skill in the art will appreciate that, in some embodiments, a therapeutically effective amount for treatment may be formulated and/or administered in a single dose. In some embodiments, a therapeutically effective amount may be formulated and/or administered in a plurality of doses, for example, as part of a dosing regimen.

Subject: By "subject" it is meant a mammal, e.g., a human. In some embodiments, a subject is suffering from a relevant disease, disorder or condition. In some embodiments, a subject is susceptible to a disease, disorder, or condition. In some embodiments, a subject displays one or more signs or symptoms or characteristics of a disease, disorder or condition. In some embodiments, a subject does not display any symptom, sign or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

T cell inactivation. As used herein, the term T cell inactivation refers to a non-responsive phenotype in a $CD4^+$ or $CD8^+$ T cell, including Treg cells which are $CD4^+CD25^+$, where the cell does not normally respond to activation signals. Unless specifically noted, the $CD4^+$ or $CD8^+$ T cell, usually a $CD4^+$ Treg cell, is a previously stimulated T cell, i.e. a cell other than a naïve T cell. As is known in the art, a naive T cell (or Th0 cell) is a T cell that has differentiated in bone marrow, and successfully undergone the positive and negative processes of central selection in the thymus. A naive T cell is considered mature but is distinguished from activated T cells or memory T cells, as it is has not yet encountered cognate antigen in the periphery. Naive T cells may be characterized by the surface expression of L-selectin (CD62L); the absence of the activation markers CD25, CD44 or CD69; and the absence of memory markers, such as the edited CD45 isoforms. In the naive state, T cells are thought to be quiescent and non-dividing.

DETAILED DESCRIPTION

Provided herein are methods of treating a disorder in a subject in need thereof, comprising administering to the subject a low dose of IL-2 and an NAE inhibitor. In some embodiments, the disorder is an autoimmune disorder, or an inflammatory disease like allergy or GVHD. Further provided are compositions comprising IL-2 and an NAE inhibitor for use in the methods described herein.

Methods of administration may include, without limitation, systemic administration or intra-lesional administration. Administration may be repeated as necessary for treatment of one or more disorders as described herein, including long term treatment of the condition by over an extended period of time. For example, in some embodiments, the NAE inhibitor and IL-2 may be co-administered as described herein for at least a month, for at least 300 days per year, for at least two years, or for the rest of the subject's life. In some embodiments, co-administration is at least once per day. In some embodiments, the IL-2 and NAE inhibitor are administered in a single dosage form. In other embodiments, the IL-2 and NAE inhibitor are administered as separate dosage forms. Co-administration of separate dosage forms may include administration at the same time (e.g., simultaneously), or close in time, for example administration of separate dosage forms within 30 min or less of each other, within 20 min or less of each other, within 15 min or less of each other, within 10 min or less of each other, or within 5 min or less of each other. In some embodiments, co-administration includes the administration of separate dosage wherein the administration is separated by greater than 30 min, greater than 1 hour, greater than 6 hours, greater than 12 hours, greater than 18 hours, or greater than a day.

In some embodiments, co-administration of IL-2 and an NAE inhibitor as described herein (such as co-administration as separate dosage forms) includes administration of one active agent (such as IL-2) within about a period of about 45 days, about 30 days, about 21 days, about 14 days, about 10 days, about 8 days, about 7 days, about 6 days, about 5 days, about 4 days, about 3 days, about 2 days, about 1 day or substantially the same day as the second active agent (such as the NAE inhibitor). In some embodiments the IL-2 is administered prior to the NAE inhibitor. In some embodiments the IL-2 is administered after the NAE inhibitor.

The IL-2 administered according to the methods described herein may come from any appropriate source. The term "IL-2" designates any source of IL-2, including mammalian sources such as e.g., human, mouse, rat, primate, and pig, and may be native or obtained by recombinant or synthetic techniques, including recombinant IL-2 polypeptides produced by microbial hosts. IL-2 may be or comprise the native polypeptide sequence or can be an active variant of the native IL-2 polypeptide. Preferably the IL-2 polypeptide or active variant is derived from a human source, and includes recombinant human IL-2, particularly recombinant human IL-2 produced by microbial hosts.

Active variants of IL-2 have been disclosed in the literature. Variants of the native IL-2 can be fragments, analogues, and derivatives thereof. By "fragment" is intended a polypeptide comprising only a part of the intact polypeptide sequence. An "analogue" designates a polypeptide comprising the native polypeptide sequence with one or more amino acid substitutions, insertions, or deletions. Muteins and pseudopeptides are specific examples of analogues, IL-2 N88R is a specific mutein with diminished binding to the intermediate affinity IL-2R βγ. "Derivatives" include any modified native IL-2 polypeptide or fragment or analogue thereof, such as glycosylated, phosphorylated, fused to another polypeptide or molecule, polymerized, etc., or through chemical or enzymatic modification or addition to improve the properties of IL-2 (e.g., stability, specificity, etc.). Active variants of a reference IL-2 polypeptide generally have at least 75%, preferably at least 85%, more preferably at least 90% amino acid sequence identity to the amino acid sequence of the reference IL-2 polypeptide.

Methods for determining whether a variant IL-2 polypeptide is active are available in the art and are specifically described in the present invention. An active variant is, most preferably, a variant that activates Tregs. Examples of IL-2 variants are disclosed, for instance, in EP109748, EP136489, U.S. Pat. No. 4,752,585; EP200280, or EP118, 617.

Preferably a recombinant IL-2 is used i.e., an IL-2 that has been prepared by recombinant DNA techniques. The host organism used to express a recombinant DNA encoding IL-2 may be prokaryotic (a bacterium such as $E.$ $coli$) or eukaryotic (e.g., a yeast, fungus, plant insect or mammalian cell). Processes for producing IL-2 have been described e.g., in U.S. Pat. Nos. 4,656,132; 4,748,234; 4,530,787; or U.S. Pat. No. 4,748,234, incorporated herein by reference. In a preferred embodiment, the invention uses an IL-2 of human origin, or an active variant thereof, more preferably produced recombinantly. A nucleotide and an amino acid sequence of human IL-2 are disclosed, for instance, in Genbank ref 3558 or P60568, respectively. The invention more preferably uses a human IL-2. IL-2 for use in the present invention may be in essentially pure form, e.g., at a purity of 95% or more, further preferably 96, 97, 98 or 99% pure.

IL-2 is commercially available, including for pharmaceutical uses, and it is authorized for use in human patients. Suitable commercial forms include, e.g., Proleukin™, a recombinant, human IL-2 composition, Aldesleukin™, an unglycosylated des-alanyl-1, serine-125 human interleukin-2 produced in $E.$ $coli$. Roncoleukin™, recombinant human IL-2 produced in yeast.

Provided herein is a method of administering interleukin-2 at a low dose in combination with an NAE inhibitor in the treatment of an autoimmune, an immune-related or an inflammatory disorder. A low dose of interleukin-2 (IL-2) is sufficient to expand regulatory T lymphocytes (Tregs) without substantially inducing effector T lymphocytes (Teffs), as distinct from a high dose that is sufficient to expand Teffs. A low dose of IL-2 is generally at least about 10-fold lower than a conventional high dose, (where a high dose may be, for example, from about 700 IU/kg/day, or from about $50\times10^6$ to $150\times10^6$ IU/day for an average human body weight). Dosage ranges described herein are provided as the dose that is administered in a one day period of time, in terms of the body surface area (m$^2$), and international units (IU). A daily dose may be fractionated into 1, 2, 3, or 4 separate doses over a day.

A low dose of IL-2 is administered at a dose of about $0.05\times10^6$ to not more than about $5\times10^6$ international unit (IU)/m$^2$/day, not more than about $4\times10^6$ IU/m$^2$/day, not more than about $3\times10^6$ IU/m$^2$/day, not more than about $2\times10^6$ IU/m$^2$/day, not more than about $1\times10^6$ IU/m$^2$/day. Preferably the dose is at least about $0.1\times10^6$ IU/m$^2$/day, at least about $0.2\times10^6$ IU/m$^2$/day, at least about $0.3\times10^6$ IU/m$^2$/day; and may be from about $0.4\times10^6$ IU/m$^2$/day, $0.5\times10^6$ IU/m$^2$/day, $0.6\times10^6$ IU/m$^2$/day, $0.7\times10^6$ IU/m$^2$/day, $0.8\times10^6$ IU/m$^2$/day, $0.9\times10^6$ IU/m$^2$/day, $1\times10^6$ IU/m$^2$/day, $2\times10^6$ IU/m$^2$/day.

The treatment may preferably comprise a course wherein interleukin-2 is administered in a dose once per day (or fractionated into multiple doses over the day), and may be administered for at least 3 consecutive days, for 3 to 7 consecutive days, for 4 to 5 consecutive days, etc. Treatment may be maintained for extended period of time, e.g. over one month, 2 months, 6 months, 1 year, 2 years or longer. The dose can be administered daily, every 2 days, every 3 days, twice per week, once per week, every 2 weeks, or once or more a month. In some embodiments, the IL-2 is administered once per day, once every 2 days, once every 3 days, twice per week, once per week, once every 2 weeks, or once or more a month.

In one embodiment, the treatment comprises a course wherein an initial dose in a range disclosed above is administered once or twice a day during at least 3 consecutive days, preferably during 3 to 7 consecutive days, still preferably 4 to 5 consecutive days, followed by a maintenance dose after one to three weeks, which maintenance dose can be repeated every one to three weeks.

IL-2 for the purposes of the present invention is usually administered at a dose of D/10 to 20×D, preferably D/5 to 10×D, wherein D is the minimal dose triggering up-regulation of expression of CD25 in Treg. Preferably the up-regulation of expression of CD25 is at least 33%, preferably at least 50%, where up-regulation of CD25 can be determined by, for example, antibody staining and flow cytometry analysis of peripheral blood T cells for expression of CD25, e.g. by analysis of CD4$^+$ cells in peripheral blood for upregulation of CD25.

The methods disclosed herein include co-administering an NAE inhibitor with a low dose of IL-2 to a subject in need thereof, to treat a disorder in the subject. Ubiquitin (Ub) and ubiquitin-like (Ubl) proteins, such as neural precursor cell-expressed developmentally downregulated 8 (NEDD8) are essential mediators of cellular function. Through a cascade of three enzymatically catalyzed events, Ub/Ubls are conjugated to target proteins, designating them for various fates such as degradation, translocation, signaling, and regulation of transcriptional activity. NEDD8-labeled proteins play a crucial role in the assembly and function of the largest family of E3 Ub ligases, the cullin ring ligases (CRL). NEDDylated cullin proteins serve as a scaffold for the assembly of the CRL and enhance CRL efficiency by increasing the recruitment of Ub-E2 complexes and assisting in their most efficient positioning relative to the substrate to be labeled. These CRLs are therefore responsible for the ubiquitination and targeted degradation of a plethora of proteins within the cell. Elevated levels of NEDDylation have been observed in aggressively proliferating malignant cells and have thus been identified as a promising target for cancer therapeutics.

Examples of NEDD8 activating enzyme (NAE) inhibitors that may be used according to the methods and compositions described herein include those listed in Table 1 below, or pharmaceutically acceptable salts thereof.

TABLE 1

| Name | Structure | Activity |
|---|---|---|
| | Inhibitors of NAE | |
| MLN4924/TAK924 | 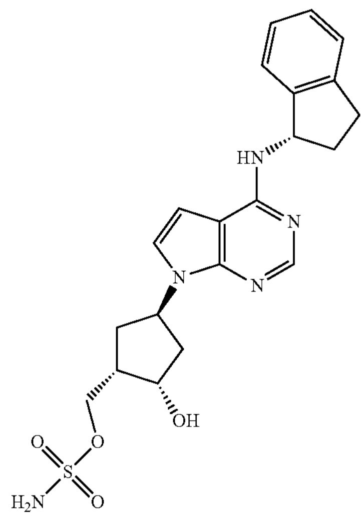 [SMILES: NS(=O)(=O)OC[C@@H]1C[C@@H](n2ccc3c(N[C@H]4CCc5ccccc54)ncnc32)C[C@@H]1O] | $IC_{50} = 0.004$ μM |
| MLN7243 | 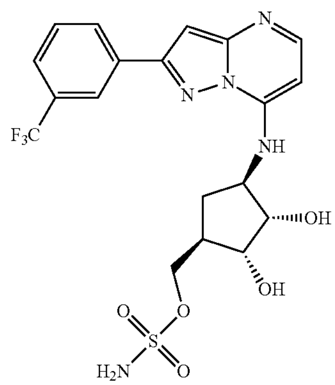 [SMILES: NS(=O)(=O)OC[C@H]1C[C@@H](Nc2ccnc3cc(-c4cccc(C(F)(F)F)c4)nn23)[C@H](O)[C@@H]1O] | $IC_{50} = 0.001$ μM |
| TAS 1 | 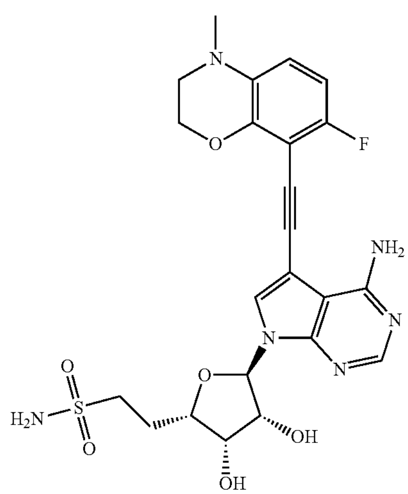 [SMILES: CN1CCOc2c1ccc(F)c2C#Cc1cn([C@@H]2O[C@@H](CCS(N)(=O)=O)[C@@H](O)[C@H]2O)c2ncnc(N)c12] | $IC_{50} = 1.0$ nM |

TABLE 1-continued

Inhibitors of NAE

| Name | Structure | Activity |
| --- | --- | --- |
| TAS 2 | 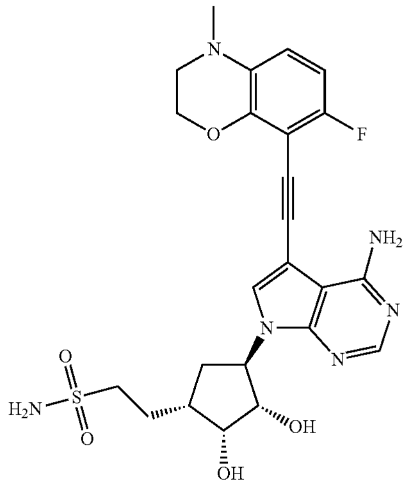 [SMILES: CN1CCOc2c1ccc(F)c2C#Cc1cn([C@@H]2C[C@@H](CCS(N)(=O)=O)[C@@H](O)[C@H]2O)c2ncnc(N)c12] | IC$_{50}$ = 20.0 nM |
| ABPA3 | 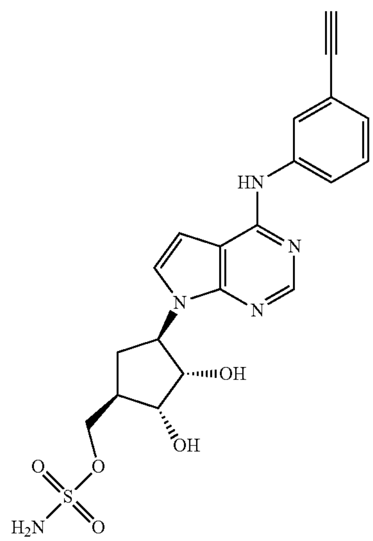 [SMILES: C#Cc1cccc(Nc2ncnc3c2ccn3[C@@H]2C[C@H](COS(N)(=O)=O)[C@@H](O)[C@H]2O)c1] | IC$_{50}$ = TBD |
| Benzothiazole | 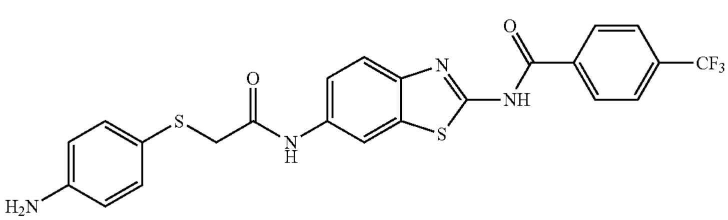 [SMILES: Nc1ccc(SCC(=O)Nc2ccc3nc(NC(=O)c4ccc(C(F)(F)F)cc4)sc3c2)cc1] | IC$_{50}$ = 0.1 μM |
| Deoxyvasicinone derivative | 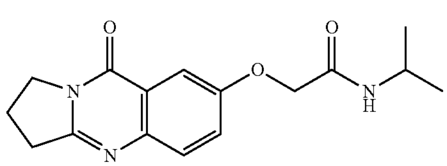 [SMILES: CC(C)NC(=O)COc1ccc2nc3n(c(=O)c2c1)CCC3] | IC$_{50}$ = 0.27 μM |
| 2,3-dihydropyrrolo[2,1-b]quinazolin-9(1H)-one | 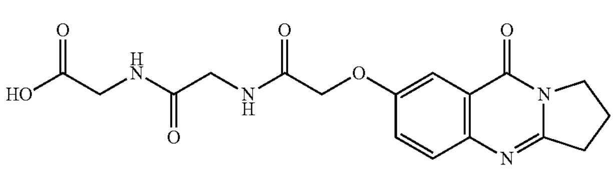 [SMILES: O=C(O)CNC(=O)CNC(=O)COc1ccc2nc3n(c(=O)c2c1)CCC3] | ? |

TABLE 1-continued

Inhibitors of NAE

| Name | Structure | Activity |
| --- | --- | --- |
| Coumarin | | IC$_{50}$ = 2.0 μM |
| Piperacillin | 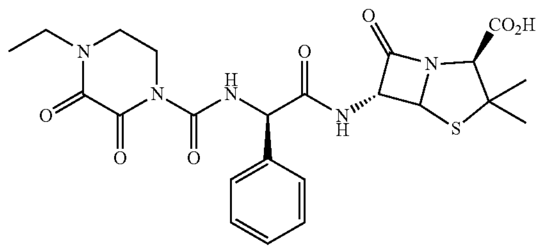 [SMILES: CCN1CCN(C(=O)N[C@@H](C(=O)N[C@@H]2C(=O)N3C2SC(C)(C)[C@@H]3C(=O)O)c2ccccc2)C(=O)C1=O] | IC$_{50}$ = 1.0 μM |
| M22 | 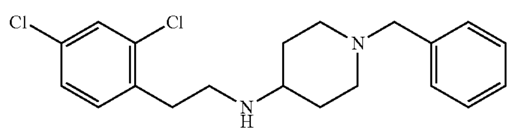 [SMILES: Clc1ccc(CCNC2CCN(Cc3ccccc3)CC2)c(Cl)c1] | IC$_{50}$ = 9.0 μM |
| 6,6'-Biapigenin | 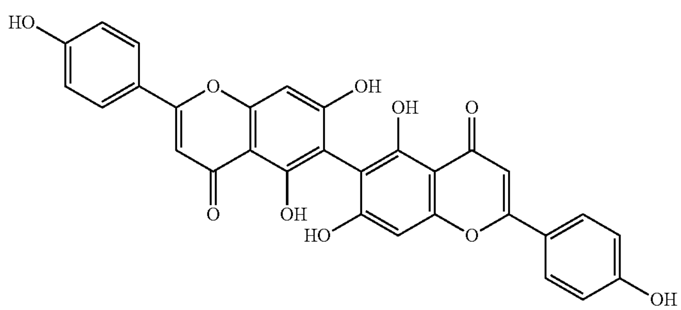 [SMILES: O=c1cc(-c2ccc(O)cc2)oc2cc(O)c(-c3c(O)cc4oc(-c5ccc(O)cc5)cc(=O)c4c3O)c(O)c12] | IC$_{50}$ = TBD |
| Coumarin | | IC$_{50}$ = TBD |
| Deoxyvasicinone derivative | 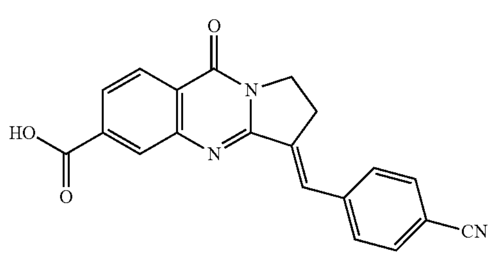 [SMILES: N#Cc1ccc(/C=C2\CCn3c2nc2cc(C(=O)O)ccc2c3=O)cc1] | IC$_{50}$ = TBD |

TABLE 1-continued

Inhibitors of NAE

| Name | Structure | Activity |
|---|---|---|
| Thieno-pyridine | (structure) | $IC_{50}$ = TBD |
| Imidazo-pyrimidine | (structure) | $IC_{50}$ = TBD |
| Imidazolium-quinoxaline | (structure) | $IC_{50}$ = TBD |

The AMP mimetic, 1S,2S,4R)-4-(4-(((1S)-2,3-dihydro-1H-inden-1-ylamino)-7H-pyrrolo[2,3-d]-pyrimidin-7-yl)-2-hydroxycyclopentyl)methyl sulfamate, also known as MLN4924, is an inhibitor of NEDD8-activating enzyme (NAE). Related compounds are disclosed in ACS Med Chem Lett. Aug. 11, 2011; 2(8): 577-582, herein specifically incorporated by reference, and may alternatively be used in the methods of the invention. Inhibition of NAE has been previously shown to induce cancer cell death and inhibit the growth of tumors in xenograft models. See, e.g., T. A. Soucy et al., Nature, 2009, 458, 732-737; T. A. Soucy et al., Clin. Cancer Res., 2009, 15 (12), 3912-3916; and J. E. Brownell et al., Mol. Cell., 2010, 37 (1), 102-111, each of which is hereby incorporated by reference herein in its entirety. MLN4924, pharmaceutical compositions of MLN4924, processes for its synthesis, and polymorphic forms have been described previously. See, e.g., U.S. patent application Ser. No. 11/700,614 (Publ. No. 2007/0191293), Ser. No. 12/221,399 (Publ. No. 2009/0036678) and Ser. No. 12/779,331 (Publ. No. 2011/0021544), each of which is hereby incorporated by reference herein in its entirety.

Compounds useful in the present invention include those described herein in any of their pharmaceutically acceptable forms, including isomers such as diastereomers and enantiomers, salts, and solvates thereof, as well as racemic mixtures of the compounds described herein.

The NAE inhibitor co-administered with the IL-2 in the methods described herein may be, for example, any one of the NAE inhibitors listed in Table 1 above. In various embodiments, the invention comprises treating autoimmune and inflammatory disease by administering an NAE inhibitor, such as MLN4924 or one of the inhibitors specifically disclosed in Table 1, for example by infusion, wherein the effective daily dose is less than or equal to about 1000 mg/m$^2$, and greater than or equal to about: 0.1 mg/m$^2$, 0.5 mg/m$^2$, 1 mg/m$^2$, 5 mg/m$^2$, 10 mg/m$^2$, 25 mg/m$^2$, 50 mg/m$^2$ or 100 mg/m$^2$; less than or equal to about 500 mg/m$^2$, and greater than or equal to about: 10 mg/m$^2$, 25 mg/m$^2$, 50 mg/m$^2$, 75 mg/m$^2$, 100 mg/m$^2$, 125 mg/m$^2$, 150 mg/m$^2$, 175 mg/m$^2$, 200 mg/m$^2$ or 250 mg/m$^2$; or less than or equal to the maximum tolerated dose (MTD), and greater than or equal to about: 0.1 mg/m$^2$, 0.5 mg/m$^2$, 1 mg/m$^2$, 10 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$ or 300 mg/m$^2$. In some such embodiments of combination therapy, the invention comprises administering the inhibitor daily, every other day, twice weekly, or weekly, where the administration is on the same day or a different day as low dose IL-2 administration.

In some embodiments the invention comprises administering the NAE inhibitor daily, every other day, twice weekly, or weekly. Administration of the NAE inhibitor may be at the same time as low dose IL-2 administration; or may be administered other than a day when low dose IL-2 is administered, e.g. each administered every other day. In some embodiments, the NAE inhibitor is administered once per day, once per every other day, twice per week, or once per week.

The compositions and methods provided herein may be used for the treatment of autoimmune, serious allergic, or inflammatory disease, including without limitation, SLE, Type I diabetes (T1D), RA, MS, graft vs. host disease, inflammatory bowel diseases etc., by the administration to a patient in need thereof an effective dose of an NAE inhibitor combined with a low dose IL-2.

In some embodiments the inhibitor of Treg IL-2R desensitization is a small molecule drug. Is some embodiments the drug is a NAE inhibitor. In other embodiments the combination provides for a synergistic effect, where the combination of the inhibitor of Treg IL-2R desensitization and low dose IL-2 provides an effect that is greater than the sum of either the inhibitor of Treg IL-2R desensitization or low dose IL-2 administered as a single agent.

Regulatory CD4 T cells (Tregs) that express the high affinity IL-2R bind and respond to wild type IL-2 at concentrations at least 100-fold lower than do resting CD4 T cells that express the intermediate affinity beta gamma complex IL-2R. In addition to the marked difference in affinity of the two receptors for IL-2, signaling through the IL-2R in the Tregs predominantly phosphorylates one of two isoforms of STAT5, STAT5b through activated pJAK1. Conventional CD4 T cells use their IL-2R to activate the other isoform, STAT5a by pJAK1. Normally, cytokine receptor signaling is rapidly terminated by inactivating the kinase activity. This pathway is negatively regulated on multiple levels. Protein tyrosine phosphatases can remove phosphates from cytokine receptors and activated STATs.

More recently identified suppressors of cytokine signaling (SOCS) were shown to inhibit STAT phosphorylation by binding and inhibiting JAKs or competing with STATs for phosphotyrosine binding sites on cytokine receptors. In the case of the high affinity IL-2R on Tregs, pJAK1 activates STAT5 and the usual inactivation of pJAK1 by SOCS3 that is seen in conventional CD4 T cells is modulated in Tregs. Normally, SOCS3 both binds to activated JAK1 to inhibit its phosphorylation of STAT5 and then forms a multi-component cullin ring ligase (CRL) protein complex consisting of SOCS3, elongin, Cullin5, RBX and a ubiquitin transferase (E2). This CRL complex requires neddylation of Cullin5 by NEDD8 to function as an E3 ligase. Tregs uniquely and constitutively express a protein, the gene related to anergy in lymphocytes (GRAIL) that is itself a ubiquitin E3 ligase that competes for the same target lysine on Cullin5 that is the target of NEDD8 neddylation. By ubiquitinating this lysine (Lys 724 in murine Tregs) on Cullin5, GRAIL ubiqutination competes with neddylation of this lysine thus inhibiting the E3 ligase activity of the SOCS3-elongin-Cullin5 CRL complex and allowing pJAK1 to continue to function as a kinase to phosphorylate STAT5. Prolonged activity of pSTAT5 is seen in Tregs that use GRAIL to block the inactivation of pJAK1 and this leads to the pSTAT5b transcription of the Treg centric transcriptome (Kanai, Jenks and Nadeau Front Immunol (2012) 14; 3:234; Yao et al. (2006) PNAS 24; 103(4):1000-5).

In some embodiments, an individual is selected for treatment with an NAE inhibitor and low dose IL-2 combination therapy because the individual shows a defect in IL-2R desensitization, GRAIL expression, etc. For example, a sample of Treg cells from the individual may be contacted with a low dose of IL-2, and the phosphorylation of STAT5 in response measured, where relative levels of low dose IL-2 induced pSTAT5 are reduced (relative to healthy controls) in individuals that may be selected for treatment.

Specific conditions of interest include systemic lupus erythematosus (SLE), an autoimmune disease characterized by polyclonal B cell activation, which results in a variety of anti-protein and non-protein autoantibodies (see Kotzin et al. (1996) Cell 85:303-306 for a review of the disease). SLE is a difficult disease to study, having a variable disease course characterized by exacerbations and remissions. For example, some patients may demonstrate predominantly skin rash and joint pain, show spontaneous remissions, and require little medication. The other end of the spectrum includes patients who demonstrate severe and progressive kidney involvement (glomerulonephritis) that requires therapy with high doses of steroids and cytotoxic drugs such as cyclophosphamide.

It appears that multiple factors contribute to the development of SLE. Several genetic loci may contribute to susceptibility, including the histocompatibility antigens HLA-DR2 and HLA-DR3. The polygenic nature of this genetic predisposition, as well as the contribution of environmental factors, is suggested by a moderate concordance rate for identical twins, of between 25 and 60%.

Disease manifestations result from recurrent vascular injury due to immune complex deposition, leukothrombosis, or thrombosis. Additionally, cytotoxic antibodies can mediate autoimmune hemolytic anemia and thrombocytopenia, while antibodies to specific cellular antigens can disrupt cellular function. An example of the latter is the association between anti-neuronal antibodies and neuropsychiatric SLE.

Evaluation of clinical progress in treatment may utilize art-recognized criteria for the classification of systemic lupus erythematosus, where successful treatment may stabilize or reduce one of more of the known clinical criteria. Known clinical criteria include: 1. Malar rash: Fixed erythema, flat or raised, over the malar eminences, tending to spare the nasolabial folds. 2. Discoid rash: Erythematous raised patches with adherent keratotic scaling and follicular plugging; atrophic scarring may occur in older lesions. 3. Photosensitivity: Skin rash as a result of unusual reaction to sunlight, by patient history or physician observation. 4. Oral ulcers: Oral or nasopharyngeal ulceration, usually painless, observed by a physician 5. Arthritis: Non-erosive arthritis involving two or more peripheral joints, characterized by tenderness, swelling, or effusion 6. Serositis: a) Pleuritis—convincing history of pleuritic pain or rub heard by a physician or evidence of pleural effusion OR b) Pericarditis—documented by ECG or rub or evidence of pericardial effusions 7. Renal disorder: a) Persistent proteinuria greater than 0.5 grams per day or greater than 3+ if quantitation not performed OR b) Cellular casts—may be red cell, hemoglobin, granular, tubular, or mixed 8. Neurologic disorder: a) Seizures—in the absence of offending drugs or known metabolic derangements OR b) Psychosis—in the absence of offending drugs or known metabolic derangements 9. Hematologic disorder: a) Hemolytic anemia—with reticulocytosis OR b) Leukopenia—less than 4000/mm$^3$ total on two or more occasions OR c) Lymphopenia—less than 1500/mm$^3$ on two or more occasions OR d) Thrombocytopenia—less than 100,000/mm$^3$ in the absence of offending drugs 10. Immunologic disorder: a) Anti-DNA: antibody to native DNA in abnormal titer OR b) Anti-Sm: presence of antibody to Sm or nuclear antigen OR c) Positive finding of antiphospholipid antibodies based on (1) an abnormal serum level of IgG or IgM anti-cardiolipin antibodies; (2) a positive test result for lupus anticoagulant using a standard method, or (3) a false positive serologic test for syphilis known to be positive for at least 6 months and confirmed by *Treponema pallidum* immobilization or fluorescent treponemal antibody absorption test. 11. Antinuclear antibody: An abnormal titer of antinuclear antibody by immunofluorescence or an equivalent assay at any point in time and in the absence of drugs known to be associated with "drug-induced lupus" syndrome.

Thus, in some embodiments, provided herein is a method of treating SLE in a subject in need thereof, comprising co-administering to the subject an NAE inhibitor and low dose IL-2. In certain embodiments, the NAE inhibitor is one of the compounds listed in Table 1.

Another condition of interest for treatment is rheumatoid arthritis. Degenerative joint diseases may be inflammatory, as with seronegative spondylarthropathies, e.g. ankylosing spondylitis and reactive arthritis; and rheumatoid arthritis. The degenerative joint diseases have a common feature, in that the cartilage of the joint is eroded, eventually exposing the bone surface. Destruction of cartilage begins with the degradation of proteoglycan, mediated by enzymes such as stromelysin and collagenase, resulting in the loss of the ability to resist compressive stress. Alterations in the expression of adhesion molecules, such as CD44 (Swissprot P22511), ICAM-1 (Swissprot P05362), and extracellular matrix protein, such as fibronectin and tenascin, follow. Eventually fibrous collagens are attacked by metalloproteases, and when the collagenous microskeleton is lost, repair by regeneration is impossible. There is significant immunological activity within the synovium during the course of inflammatory arthritis. While treatment during early stages is desirable, the adverse symptoms of the disease may be at least partially alleviated by treatment during later stages. Clinical indices for the severity of arthritis include pain, swelling, fatigue and morning stiffness, and may be quantitatively monitored by Pannus criteria. Disease progression in animal models may be followed by measurement of affected joint inflammation. Therapy for inflammatory arthritis may combine the subject treatment with conventional treatment.

Thus, in some embodiments, provided herein is a method of treating rheumatoid arthritis in a subject in need thereof, comprising co-administering to the subject an NAE inhibitor and low dose IL-2. In certain embodiments, the NAE inhibitor is one of the compounds listed in Table 1.

In some embodiments, the combination therapy is useful in the treatment of multiple sclerosis. A quantitative increase in myelin-autoreactive T cells with the capacity to secrete IFN-gamma or IL-17 is associated with the pathogenesis of MS and EAE, suggesting that autoimmune inducer/helper T lymphocytes in the peripheral blood of MS patients may initiate and/or regulate the demyelination process in patients with MS. The overt disease is associated with muscle weakness, loss of abdominal reflexes, visual defects and paresthesias. During the presymptomatic period there is infiltration of leukocytes into the cerebrospinal fluid, inflammation and demyelination. Family histories and the presence of the HLA haplotype DRB1*1501, DQA1*0102, DQB*0602 are indicative of a susceptibility to the disease. Markers that may be monitored for disease progression are the presence of antibodies in the cerebrospinal fluid, "evoked potentials" seen by electroencephalography in the visual cortex and brainstem, and the presence of CNS or spinal cord defects by MRI or computerized tomography. Treatment during the early stages of the disease will slow down or arrest the further loss of neural function.

Thus, in some embodiments, provided herein is a method of treating multiple sclerosis in a subject in need thereof, comprising co-administering to the subject an NAE inhibitor and low dose IL-2. In certain embodiments, the NAE inhibitor is one of the compounds listed in Table 1.

In some embodiments, human Type One (insulin dependent) diabetes mellitus (T1D) can be treated. The disease is a cell-mediated autoimmune disorder leading to destruction of insulin-secreting β cells and overt hyperglycemia. T lymphocytes invade the islets of Langerhans, and specifically destroy insulin-producing beta-cells. The depletion of β cells results in an inability to secrete insulin to regulate levels of glucose in the blood. Overt diabetes occurs when the level of glucose in the blood rises above a specific level, usually about 250 mg/dl.

In humans a long presymptomatic period precedes the onset of T1D. During this period there is a gradual loss of pancreatic beta cell function. The disease progression may be monitored in individuals diagnosed by family history and genetic analysis as being susceptible. The most important genetic effect is seen with genes of the major histocompatibility locus (IDDM1), although other loci, including the insulin gene region (IDDM2) also show linkage to the disease (see Davies et al, supra and Kennedy et al. (1995) Nature Genetics 9:293-298). Markers that may be evaluated during the presymptomatic stage are, the level and frequency of islet cell antibodies, islet cell surface antibodies, glucose concentration in the blood, and the plasma concentration of insulin. An increase in the number of T lymphocytes in the pancreas, islet cell antibodies and blood glucose is indicative of the disease, as is a decrease in insulin concentration and an abnormal response to orally administered glucose (OGGT). After the onset of overt hyperglycemia, patients with residual beta cell function, evidenced by the plasma persistence of insulin C-peptide, may also benefit from the subject treatment, to prevent further loss of function and potentially restore euglycemia.

Thus, in some embodiments, provided herein is a method of treating human T1D in a subject in need thereof, comprising co-administering to the subject an NAE inhibitor and low dose IL-2. In certain embodiments, the NAE inhibitor is one of the compounds listed in Table 1.

The response of an immune competent donor graft towards the host (graft versus host disease, GVHD) may be reduced by treatment with the subject synergistic combination of inhibitors. Grafts include the transplantation of cells, tissues and organs that contain immune competent cells, such as the transfusion of blood or blood components, the grafting of bone, skin, bone marrow, etc., and the transplantation of tissues of the eye, pancreas, liver, kidney, heart, brain, bowel, lung, etc. Of interest are transplantation of hematopoietic cells, e.g. bone marrow, mobilized hematopoietic stem cells in peripheral blood, etc. As used herein, a graft recipient is an individual to whom tissue or cells from another individual (donor), commonly of the same species, has been transferred, particularly where one or more of the Class I MHC antigens are different in the donor as compared to the recipient. However, in some instances xenogeneic, e.g. pig, baboon, etc., tissue, cells or organs will be involved. The graft recipient and donor are generally mammals, preferably human.

Thus, in some embodiments, provided herein is a method of treating graft versus host disease (GVHD) in a subject in need thereof, comprising co-administering to the subject an NAE inhibitor and low dose IL-2. In certain embodiments, the NAE inhibitor is one of the compounds listed in Table 1.

In some embodiments a serious allergic disease is treated, where a serious allergy is defined by allergies to environmental, insect, animal, food, drug, protein and/or carbohydrate moiety that result in a serious reaction (at any point in their life) as defined by abdominal pain, wheezing, rash over ¼ of the body, nasal congestion/occlusion, eye redness and itchiness, skin swelling and/or vomiting/nausea, anaphylaxis. Thus, in some embodiments, provided herein is a method of treating serious allergies in a subject in need thereof, comprising co-administering to the subject an NAE inhibitor and low dose IL-2. In certain embodiments, the NAE inhibitor is one of the compounds listed in Table 1, where the treatment provides a reduction in clinical signs of allergy.

As used herein, a stimulation (or induction or activation or amplification) of Treg designates any increase in proportion of Treg cells relative to Teffs, in number or in activity as tested by suppressive assays or by expression of molecules that reflect the activity of the Tregs such as pSTAT5, CD25, the alpha-chain of the IL-2 receptor, Foxp3, or GITR in a patient. The augmentation in proportion is preferably by at least about 20% as compared to the level prior to treatment, more preferably at least about 40%, even more preferably at least about 60%.

One biomarker for efficacy of low dose IL-2 is an increase in the ratio of Tregs to Teffs. In a particular and preferred embodiment, an effective treatment provides for a shift in the Treg/Teff balance towards Tregs, or an increase in the Treg/Teff ratio or an increase in the inherent regulatory capacity of Tregs from the treated subject. The total number of Treg cells as a percent of total CD4+ cells in peripheral blood may initially range from around about 1%, around about 2%, around about 3%, around about 4% around about 5% up to about 10%, about 15%, about 20% or more. The augmentation in proportion is preferably by at least about 20% as compared to the level prior to treatment, more preferably at least about 40%, even more preferably at least about 60%.

The stimulation of Treg and absence of substantial induction of Teff is preferably assessed by a measure of the ratio or the balance Treg/Teff in the treated subject. This balance is calculated e.g., based on the number of Tregs and the number of Teff in a sample from the subject. Such a balance typically increases by at least about 20% in the treated patients, more preferably by at least about 30%, at least about 40%, at least about 60%, or more relative to an untreated control. In some embodiments, administration of an NAE inhibitor and low dose IL-2 as described herein results in an increase in the Treg/Teff ratio of at least about 10%, at least about 20%, at least about 30%, at least about 40%, at least about 50%, or at least about 60%, as compared to the ratio in the subject before beginning administration.

Effective expansion of Tregs may be measured by an increase in absolute numbers of Treg cells in the patient, typically by at least about 10%, at least about 20%, at least 30% or more in number relative to the starting population. Expansion may be measured by an increase in activation markers on Treg cells, such as the intensity of CD25 or FoxP3 expression or pSTAT5, e.g. at least about 10%, at least about 20%, at least about 30% or more increase relative to an untreated control.

Alternatively an increase in Treg activity may be determined in an in vitro assay by the number of Tregs from a treated patient required to give 50% reduction in response to activating the Teffs from the same patient. In a normal patient the ratio is from about 1:2, from about 1:4, to about 1:10 Tregs to Teffs, and an increase may be by at least about 20% in the treated patients, more preferably by at least about 30%, at least about 40%, at least about 60%, or more relative to an untreated control.

The absence of substantial induction (or activation or expansion) of Teff can also be measured by measuring the number of Teff and/or the activity of Teff in samples from the treated subject. The absence of substantial induction indicates the target Teff cell population does not acquire markers of activation such as CD25, CD69, and/or HLA-DR, or as assessed by whole transcriptome analyses. An absence of Teff induction typically designates that the Teff cell population has not increased by more than 10% in said subject as a result of treatment. Detailed methods for detecting, measuring and quantifying Treg and Teff cells are known in the art.

For use in the present invention, IL-2 is present at a concentration that effectively activates Tregs without substantially activating Teffs, in combination with an inhibitor of NAE. The effective dosage can be adjusted by the practitioner, based on information contained in the present application. In particular, with the knowledge of the present invention that, in patients with autoimmune disease, IL-2 and an NAE inhibitor may be administered under conditions which do activate endogenous Tregs and which essentially do not activate Teff, the skilled person may be able to adjust dosages to each patient and condition.

The agents (NAE inhibitor and IL-2) may be administered using any acceptable method known per se in the art. Thus, for example, IL-2, or the pharmaceutical composition comprising IL-2, can be administered by any form of injection, including intravenous (IV), intramuscular (IM), or transdermal or subcutaneous (SC) injection, or by oral or nasal route as well as by topical administration (cream, droplets, etc.). or in slow release formulation. The NAE inhibitor may be administered individually without concomitant low dose IL-2, or at the same time as administered IL-2, or at staggered times, and may be administered parenterally, orally, etc. In a particular embodiment of the invention, IL-2 can be used as a sustained-release formulation, or a formulation that is administered using a sustained release device. Such devices are well known in the art, and include, for example, transdermal patches, and miniature implantable pumps that can provide for drug delivery over time in a continuous, steady-state fashion at a variety of doses to achieve a sustained-release effect. Sublingual or eye drop formulations may also be contemplated.

The agents are administered as single or combined active agents in association (e.g., in solution, suspension, or admixture) with a pharmaceutically acceptable vehicle, carrier or excipient. Suitable excipients may include any isotonic solution, saline solution, buffered solution, etc. Liquid, lyophilized, or spray-dried compositions comprising IL-2 or variants thereof are known in the art and may be prepared as aqueous or nonaqueous solutions or suspensions.

The pharmaceutical compositions may comprise appropriate stabilizing agents, buffering agents, bulking agents, or combinations thereof to minimize problems associated with loss of active agent stability and biological activity during preparation and storage. A buffering agent may be used to maintain pH of the liquid composition within an acceptable range for stability. The buffering agent may be an acid such as e.g., succinic acid, citric acid, phosphoric acid, and glutamic acid. Examples of suitable bulking agents include e.g., glycine, mannitol, or valine, or any combination thereof. Due to the hydrophobicity of certain drugs, including without limitation MLN4924, additives such as DMSO may be added to maintain the drug in solution.

Examples of inert carriers which may be used as stabilizing agents include sugars (e.g., sucrose, glucose, dextrose) and sugar alcohols, as well as amino acids. The pharmaceutical composition may additionally incorporate other stabilizing agents, such as methionine, a nonionic surfactant such as polysorbate 80, etc.

Where IL-2 is in monomeric form, it is preferred to add to the compositions an amino acid base sufficient to decrease aggregation of IL-2 during storage. The amino acid base can be an amino acid or a combination of amino acids, where any given amino acid is present either in its free base form or in its salt form. Examples of such amino acids include arginine, lysine, and aspartic acid.

In some embodiments, subjects can be treated with agents in addition to the combination of low dose IL-2 and the NAE inhibitor, including various agents known in the art and used for treatment of inflammatory disease. Additional agents may be selected from one or more of the general classes of drugs commonly used in the treatment of the disease of interest, for example corticosteroids, disease modifying drugs, antigen-specific agents, etc. Corticosteroids have a short onset of action, but many disease modifying drugs take several weeks or months to demonstrate a clinical effect. These agents include methotrexate, leflunomide (Arava™), etanercept (Enbrel™), infliximab (Remicade™), adalimumab (Humira™), anakinra (Kineret™), rituximab (Rituxan™), CTLA4-Ig (abatacept), antimalarials, gold salts, sulfasalazine, d-penicillamine, cyclosporin A, cyclophosphamide azathioprine; and the like. Corticosteroids, e.g. prednisone, methylpredisone, prednisolone, solumedrol, etc. have both anti-inflammatory and immunoregulatory activity. They can be given systemically or can be injected locally. Corticosteroids are useful in early disease as temporary adjunctive therapy while waiting for disease modifying agents to exert their effects. Corticosteroids are also useful as chronic adjunctive therapy in patients with severe disease.

Also included are interferons, e.g. beta-interferon, including without limitation the currently approved drugs AVONEX™ (IFNβ 1A), BETASERON™ (IFN-β1B); EXTAVIA™ (IFN-β1B), REBIF™ (IFNβ 1A), and bioequivalents and derivatives, e.g. pegylated derivatives, thereof. Conditions that can be treated with β-interferons include MS, EAE, etc. Such diseases can also be treated with glatiramer acetate (Copaxone). Other agents include cytokines, for example IL-1Φ; IL-4; IL-5; IL-6; IL-7; IL-8; IL-10; IL-11; IL-12; IL-13; IL-15; IL-17; IL-18; IL-20; IL-21; IL-23; and IL29.

Agents that have been found useful in treating inflammatory diseases also include statins, e.g. pravastatin, simvastatin, lovastatin, fluvastatin, atorvistatin, pitavastatin, rosuvastatin, etc. Monoclonal antibodies in use include, without limitation, ACTEMRA™ (tocilizumab); ARZERRA™ (ofatumumab); BEXXAR™ (tositumomab; $^{131}$I tositumomab); CAMPATH™ (alemtuzumab); CIMZIA™ (certolizumab pegol); HUMIRA™ (adalimumab); ILARIS™ (canakinumab); PROLIA™ (denosumab); REMICADE™ (infliximab); RITUXAN™ (rituximab); SIMPONI™ (golimumab); SIMULECT™ (basiliximab); STELARA™ (ustekinumab); TYSABRI™ (natalizumab); XGEVA™ (denosumab); XOLAIR™ (omalizumab); ZENAPAX™ (daclizumab). Monoclonal antibodies specific for amyloid include LY2062430 (solanezumab), PF-04360365, MABT5102A, bapineuzumab, gantenerumab. Other therapeutic agents of interest include lenalidomide (Revlimid); fingolimod (Gilenya); teriflunomide; cladribine; and BG-12 (Panaclar, BG-00012, FAG-201); JAK inhibitors and Syk inhibitors, which include without limitation the JAK-3 inhibitor tasocitinib (CP-690,550); Syk inhibitor fostamatinib (R788) etc.

Monitoring the influence of agents, such as IL-2 co-administered with an NAE inhibitor, on Treg disorders can be applied not only in basic drug screening, but also in clinical trials. In such clinical trials, the activity of Treg cells in a targeted tissue can be used as a biomarker for efficacy. In addition, genes that are modulated in cells by treatment with the putative agent may be identified. The levels of gene expression and protein phosphorylation can be quantified by any convenient method. In this way, the gene expression and phosphorylation pattern can serve as a marker, indicative of the physiological response of the cells to the agent. Accordingly, this response state may be determined before, and at various points during treatment of the individual with the agent (such as low dose IL-2 co-administered with an NAE inhibitor).

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

The following examples are given for purposes of illustration and not by way of limitation.

EXPERIMENTAL

Example 1

A current paradigm for the use of low dose IL-2 in treatment of these "inflammatory" diseases proposes that the high affinity of the IL-2R on the Tregs is the key to the therapeutic effect. However, Applicants have demonstrated that it is not simply affinity of the Treg IL-2R, but also the downstream signaling pathway following receptor engagement that distinguishes Treg IL-2R activation from that of conventional CD4 T cells.

Applicants have made the unexpected observation that GRAIL expression, which is important in Treg function, is markedly diminished in a majority of SLE patients examined, all of whom had diminished Treg function. The high affinity IL-2 receptor (IL-2R) on resting Tregs from normal individuals preferentially activates the phosphorylation of STAT5b, whereas 100-fold higher doses of IL-2 are required to preferentially activate phosphorylation of STAT5a in resting conventional CD4 T cells. GRAIL in Tregs from normal subjects potentiates the IL-2 induced activity of STAT5b by inhibiting the ubiquitination and degradation of pJAK1 by the SOCS3-Elongin-Cullin5 cullin ring E3 ligase complex that ubiquitinates pJAK1 and leads to its degradation in conventional CD4 T cells, thus stopping IL-2R signaling.

Neddylation is required for SOCS3-Elongin-Cullin5 E3-ligase activity, thus ubiquitination of Lys 724 (in murine Tregs) by GRAIL can delay E3 ligase activity of the SOCS-Elongin-Cullin5 E3 complex and ubiquitination of pJAK1, favoring prolonged IL-2R STAT5b signaling in the low dose IL-2 activated Tregs. Loss of STAT5b in humans can lead to defective Tregs and the development of autoimmune diseases. By inhibiting neddylation of Cullin5, the functional activity of Tregs activated by low dose IL-2 is potentiated. In support of this model, Tregs isolated from 6 SLE patients had a marked loss of pSTAR5 expression over time compared to Tregs form 6 normal control subjects activated in the same way, demonstrating the loss of inhibition of IL-2R desensitization in the SLE Tregs compared to the Tregs form normal individuals.

Figure 1B:
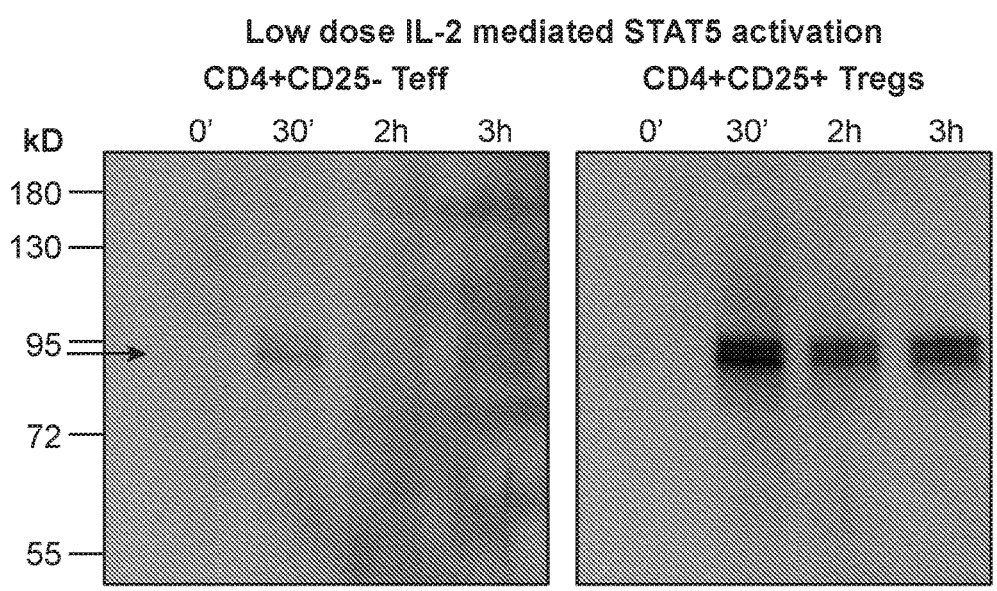

The ubiquitin E3 ligase, GRAIL, constitutively expressed in human and mouse Tregs, delays IL-2R desensitization by inhibiting the posttranslational modification (neddylation) of the cullin5 component of the SOCS3 cullin ring ligase (CRL) that degrades IL-2Rβ chain associated pJAK1 to desensitize the IL-2R to stop the signaling cascade (FIG. 1A). This observation supports a novel paradigm, that it is not simply the affinity of the Treg IL-2R that allows low dose IL-2 to function in therapy of inflammatory diseases, but also the prolonged IL-2R pJAK1 pSTAT5 signaling that ensues following Treg IL-2R engagement (FIG. 1B). Prolongation of phosphorylated STAT5 expression in the nucleus of Tregs facilitates the establishment of differentiation transcriptional programs dependent on STAT5, including T cell acquisition of FOXP3 and CD25, hallmarks of Treg differentiation, expansion and survival.

Example 2

Systemic Lupus Erythematosus

Applicants' experiments have demonstrated that the high affinity IL-2 receptor (IL-2R) on resting Tregs from normal individuals preferentially activates the phosphorylation of one of two isoforms of STAT5, STAT5b, whereas 100-fold higher doses of IL-2 are required to preferentially activate phosphorylation of the other isoform STAT5a in resting conventional CD4 T cells. GRAIL in Tregs from normal subjects potentiates the IL-2 induced activity of STAT5b by inhibiting the ubiquitination and degradation of pJAK1 through the assembly of the SOCS3-Elongin-Cullin5 complex that has E3 activity and can ubiquitinate pJAK1 and lead to its degradation. In humans and in an animal model for SLE, it is shown that there is a defect in this pathway.

Figure 2:
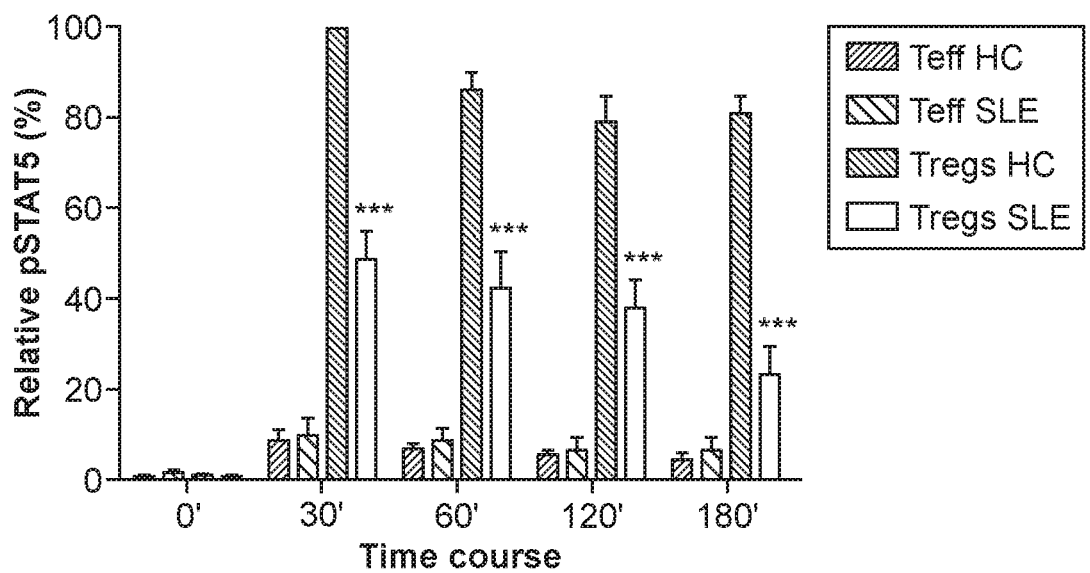
FIG. 2. Ineffective inhibition of IL-2R desensitization in SLE Tregs. Kinetics and amplitude of STAT5 phosphorylation of human Tregs (CD25+) vs human Teffs (CD24−) following exposure to low dose IL-2 (1 ng/ml) in cultures harvested at the indicated times are significantly decreased in SLE patients' Tregs compared to normal donor Tregs. (N=6 subjects per group, *** $p<0.001$ by two-way ANOVA).

In human studies, it was found that there is a defect in IL-2R desensitization in Tregs from SLE patients. Shown in FIG. 2, SLE Tregs are ineffective in inhibition of IL-2R desensitization. Kinetics and amplitude of STAT5 phosphorylation of human Tregs (CD25$^+$) vs human Teffs (CD25$^-$) following exposure to low dose IL-2 (1 ng/ml) in cultures harvested at the indicated times are significantly decreased in SLE patients' Tregs compared to normal donor Tregs.

Monoclonal anti-GRAIL antibodies have been developed to be used in SLE patient phenotyping (and potentially in other autoimmune disease states). These antibodies have been produced and can be used to quantify GRAIL expression in Tregs from normal individuals and subjects with autoimmune and inflammatory conditions. Standard anti-CD3/CD28 bead-based activation and co-culture of autologous conventional CD4 T cells with Tregs from normal and GRAIL deficient and GRAIL sufficient patients is performed to assess regulatory function using standard technology.

Figure 3:
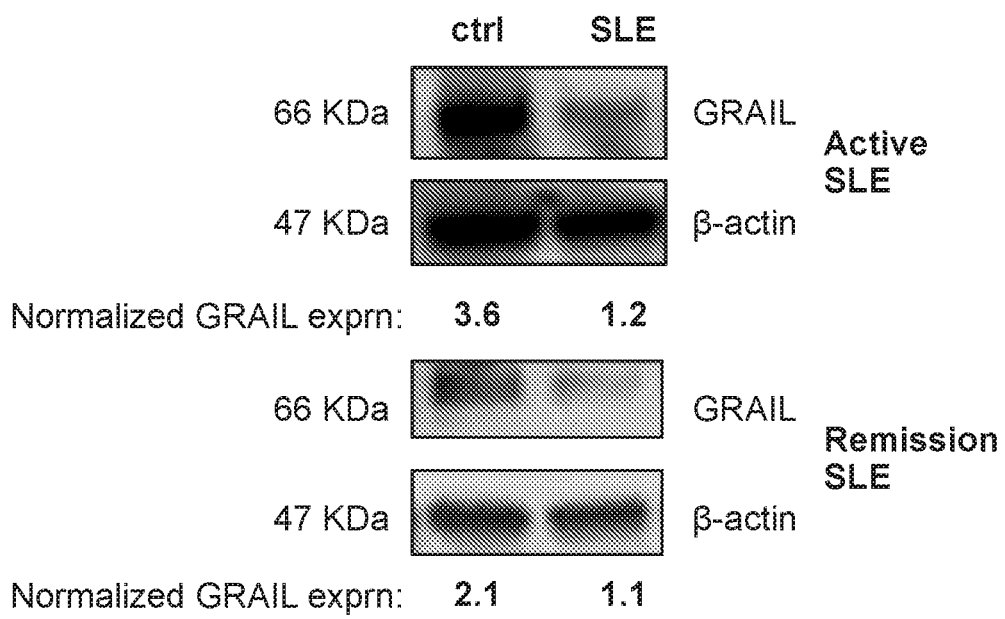
FIG. 3. Representative western blot of pSTAT5 expression of Tregs from an active untreated SLE patient and an inactive SLE patient stimulated with low dose IL-2 compared to normal control Tregs. Samples were whole cell extracts from purified Treg cells. The blot was stained with anti-GRAIL antibody and a β-actin control antibody. The GRAIL deficient SLE Tregs had a significant loss of function.

The defect in IL-2R desensitization appears to be linked to a defect in GRAIL expression. Whole cell extracts of Tregs from an SLE patient with active or inactive disease were extracted and blotted to determine the levels of GRAIL expression. It was found that a loss of GRAIL activity was associated with Treg cells from active and inactive disease. Data are shown in FIG. 3. Tregs from all SLE patients studied (n=6) compared to control health subjects (n=6) had a defect in the expected inhibition of IL-2R desensitization.

Example 3

Type One Diabetes

In patients with T1D pre-diabetic subjects that are identified before overt hyperglycemia by using autoantibody profiling and oral glucose tolerance tests in genetically at-risk subjects can be treated to reduce development of disease. An alternative embodiment of this technology is to treat subjects shortly after they have become hyperglycemic to reduce autoimmune damage to pancreatic cells and restore euglycemia.

Figure 4A:
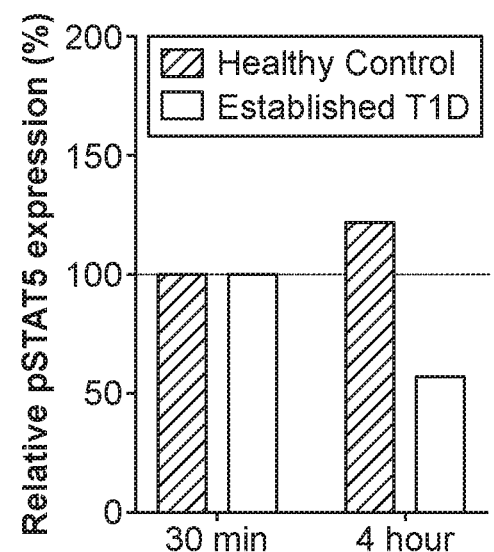
FIGS. 4A-4B. By analyzing low dose IL-2 activation of Tregs from a patient with T1D, it was possible to see a defect in inhibition of the IL-2R desensitization (a more rapid loss of pSTAT5 over time in response to low dose IL-2 in the T1D patient's cells vs normal control Tregs) (FIG. 4A). Additionally, we were able to see the ability of the NAE inhibitor given in vitro to enhance Treg function (increase pSTAT5 expression over the four-hour time course in the presence of low dose IL-2 and the NAE inhibitor compared to aliquots of the same cells activated by low dose IL-2 in the absence of the NAE inhibitor (FIG. 4B).
Figure 4B:
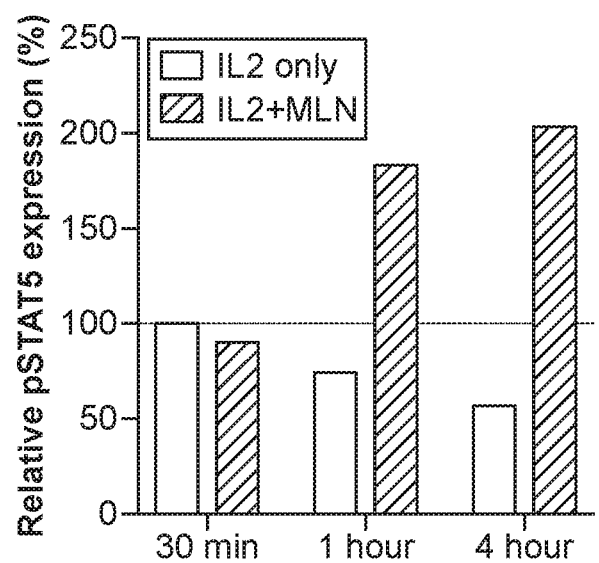

NOD mice, which develop high blood sugar around 14-16 weeks of age, were treated with a low dose of IL-2 at 100 ng/mouse delivered ip, alone or in combination with the neddylation inhibitor MLN4924 at a dose of 400 µg/mouse delivered ip. Progression to hyperglycemia was prevented by administering the combination of low dose IL-2 and MLN4924 at 12 weeks of age, a time that beta cell damage has begun to lead to hyperglycemia. In studies with Tregs from a patient with established T1D, it was demonstrated that there was a defect in inhibition of IL-2R desensitization when compared to Tregs from normal subjects, and that the defect, read out as diminished pSTAT5 expression at 4 hours in culture with low dose IL-2, could be overcome with the addition of the NAE inhibitor leading to restoration of pSTAT5 expression at 4 hours, shown in FIGS. 4A-4B.

Example 4

Combination Treatment of EAE

Figure 5A:
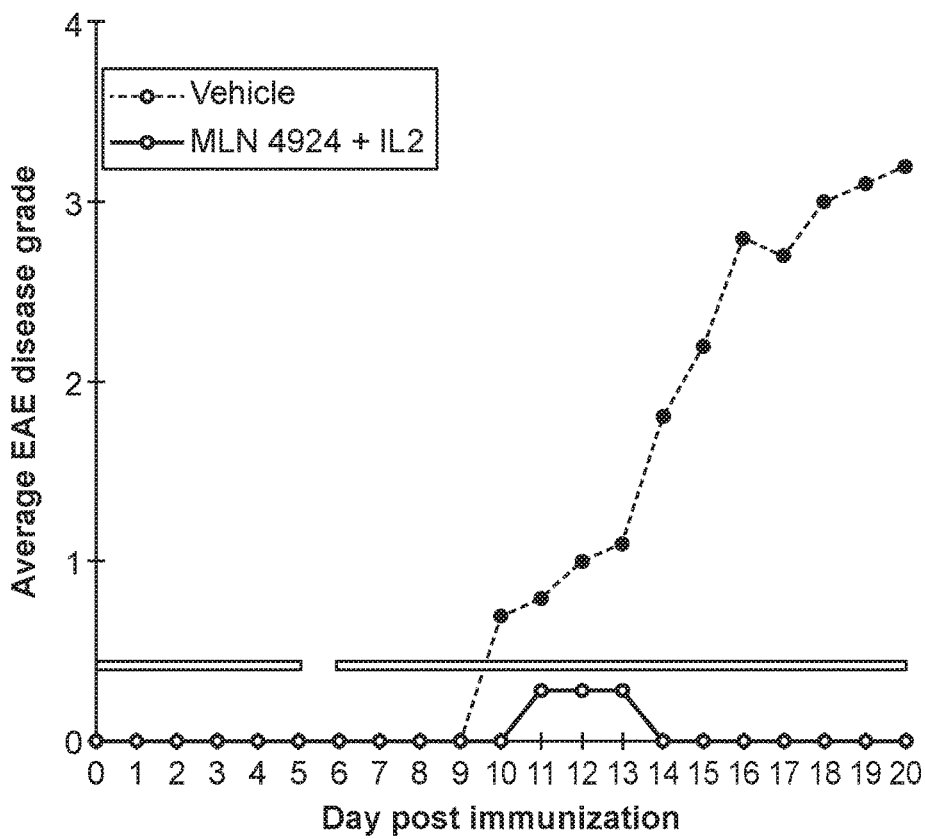
FIGS. 5A-5B. Treatment or prevention of EAE. B6 mice (groups of 10) were immunized with MOG in CFA and either treated daily for 20 days with the combination of low dose IL-2 and the NAE inhibitor beginning at the time of immunization (FIG. 5A; prevention study) or treated for 5 days after the mice had developed hemiparesis (with each drug individually or in combination), a clinical score of 2 (FIG. 5B; treatment study). The combination of the neddylation inhibitor and low dose IL-2 was significantly better than either drug alone.
Figure 5B:
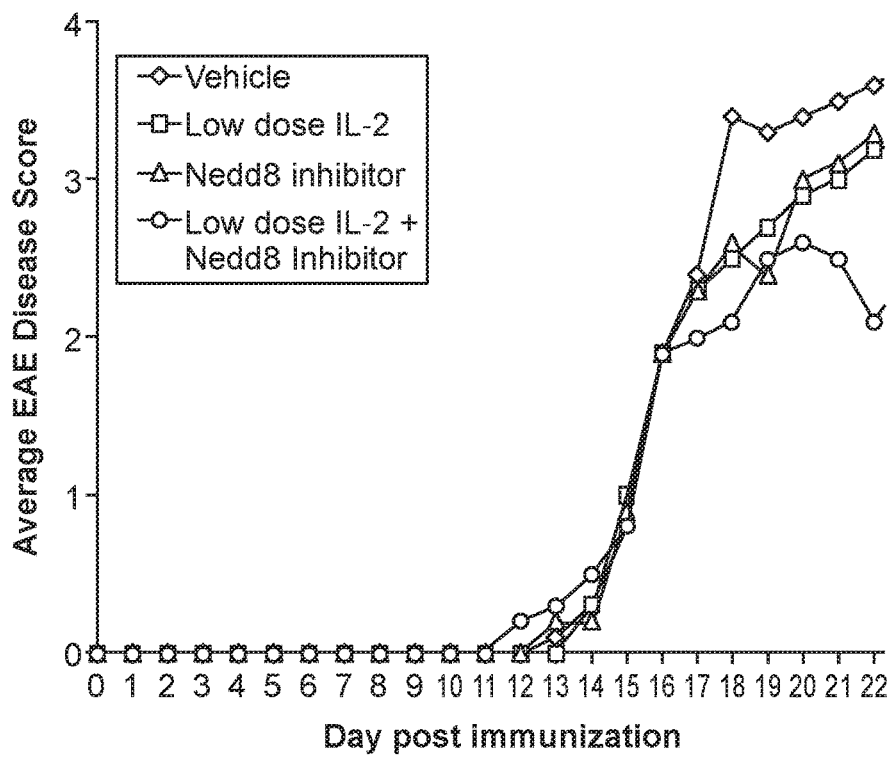

B6 mice (groups of 10) were immunized with MOG in CFA and either treated daily with a low dose of IL-2 at 100 ng/mouse delivered ip, in combination with the neddylation inhibitor MLN4924 at a dose of 400 µg/mouse delivered ip for 20 days beginning at the time of immunization (FIG. 5A; prevention study) or treated for 5 days after the mice had developed hemiparasis, a clinical score of 2 with either low dose IL-2, MLN4924, or a combination of the two (FIG. 5B; treatment study). The combination of the neddylation inhibitor and low dose IL-2 in treating disease was significantly better than either drug alone. In patients with MS, the treatment can be used to prevent progression or relapse in subjects who have been diagnosed by conventional methods to have active MS.

Example 5

Defect in Treg of Allergic Individuals

Figure 6:
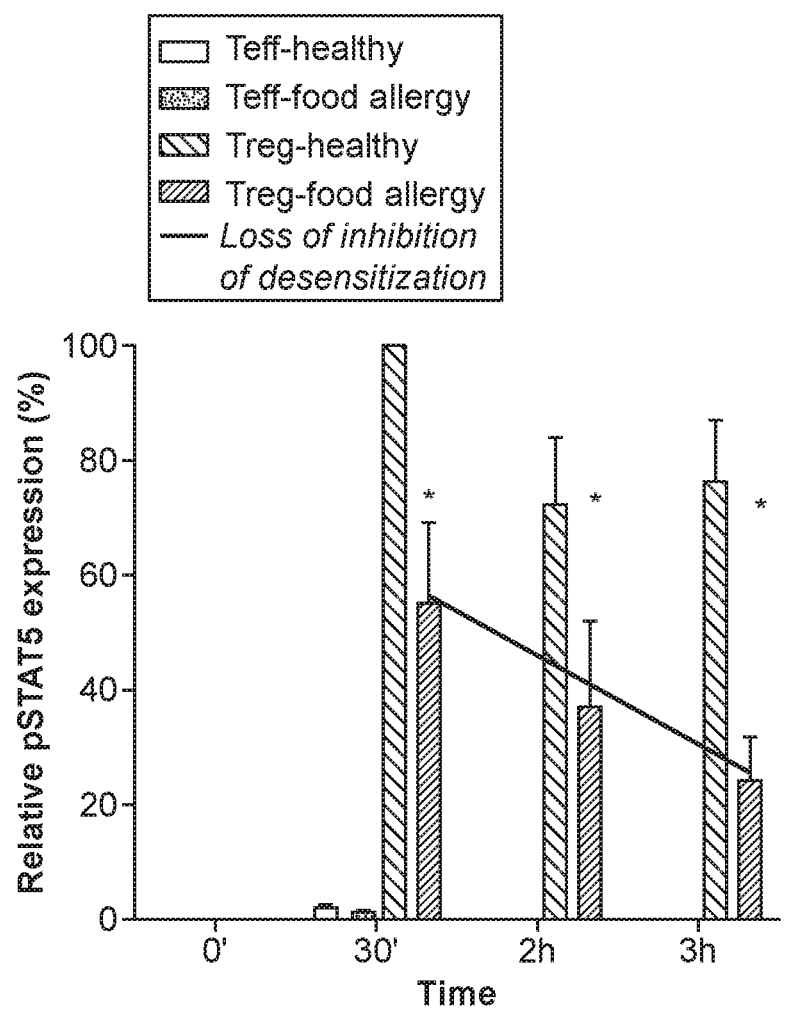
FIG. 6. pSTAT5 (% relative to pSTAT5 at 30' in Tregs purified from healthy controls) in human Teffs vs. human Tregs in healthy and allergy participants (n=3 per group) following low dose IL-2 (1 ng/ml) in cultures harvested at the indicated times. SD graphed. $p<0.05$ for * with two-way ANOVA.

Treg and Teff cells were isolated from allergic or healthy control individuals (n=3 per group). The T cell populations were separated by flow cytometry for the phenotype $CD4^+ CD25^+$ (Treg) or $CD4^+CD25^-$ (Teff). The isolated cells were placed in culture medium in the absence or presence of low dose IL-2 (1 ng/ml), and harvested as the time indicated in FIG. 6. The level of phosphorylated STAT5 (pSTAT5) was determined by binding to an antibody specific for pSTAT5. The % of phosphorylated protein relative to that of a healthy control was determined, and is graphed in FIG. 7. SD graphed. $p<0.05$ for * with two-way ANOVA. The data shows that there is a decrease in pSTAT5 in Treg cells from allergic individuals following activation with low dose IL-2.

MacKenzie D A, Schartner J, Lin J, Timmel A, Jennens-Clough M, Fathman C G, Seroogy C M. GRAIL is up-regulated in CD4+CD25+T regulatory cells and is sufficient for conversion of T cells to a regulatory phenotype. J Biol Chem. 2007 282(13):9696-702.

Seroogy C M, Soares L, Ranheim E A, Su L, Holness C, Bloom D, Fathman C G. The gene related to anergy in lymphocytes, an E3 ubiquitin ligase, is necessary for anergy induction in CD4 T cells. J Immunol. 2004 173(1):79-85

Babon J J, Nicola N A. The biology and mechanism of action of suppressor of cytokine signaling 3. Growth Factors. 2012 (4):207-19.

Williams J J, Munro K M, Palmer T M. Role of Ubiquitylation in Controlling Suppressor of Cytokine Signalling 3 (SOCS3) Function and Expression. Cells. 2014 3(2):546-62.

Rhee H W, Zou P, Udeshi N D, Martell J D, Mootha V K, Carr S A, Ting A Y. Proteomic mapping of mitochondria in living cells via spatially restricted enzymatic tagging. Science. 2013 339(6125):1328-31

Emanuele M J, Elia A E, Xu Q, Thoma C R, Izhar L, Leng Y, Guo A, Chen Y N, Rush J, Hsu P W, Yen H C, Elledge S J. Global identification of modular cullin-RING ligase substrates. Cell. 2011 147(2):459-74

Merlet J, Burger J, Gomes J E, Pintard L. Regulation of cullin-RING E3 ubiquitin-ligases by neddylation and dimerization. Cell Mol Life Sci. 2009 66(11-12):1924-38

Kanai T, Seki S, Jenks J A, Kohli A, Kawli T, Martin D P, Snyder M, Bacchetta R, Nadeau K C. Identification of STAT5A and STAT5B target genes in human T cells. PLoS One. 2014 9(1):e86790

Hwa V, Nadeau K, Wit J M, Rosenfeld R G. STAT5b deficiency: lessons from STAT5b gene mutations. Best Pract Res Clin Endocrinol Metab. 2011 (1):61-75

Tan Y C, Blum L K, Kongpachith S, Ju C H, Cai X, Lindstrom T M, Sokolove J, Robinson W H. Clin Immunol. 2014 March; 151(1):55-65.

Samantha F. Friend, Lisa K. Peterson, Eric Treacy, Adrianne L. Stefanski, Tomasz Sosinowski, Nathan D. Pennock, Allison J. Berger, Virginia D. Winn, and Leonard L. Dragone. The Discovery of a Reciprocal Relationship between Tyrosine-Kinase Signaling and Cullin Neddylation PLoS One. 2013 Oct. 4; 8(10):e75200.

Enumerated Embodiments

Embodiment 1. A method for treating an inflammatory disorder in a subject in need thereof, comprising administering to the subject:

(i) an effective dose of an NAE inhibitor; and (ii) a low dose of IL-2;

wherein administration results in an increase in one or both of the function and ratio of regulatory T lymphocyte (Treg) cells compared to effector T lymphocyte (Teff) cells in the subject, compared to the ratio in the subject prior to administration.

Embodiment 2. The method of embodiment 1, wherein the low dose of IL-2 is from about $0.05 \times 10^6$ IU/m2 to about $2 \times 10^6$ IU/m2.

Embodiment 3. The method of embodiment 1 or 2, wherein the low dose of IL-2 is from about $0.1 \times 10^6$ IU/m2 to about $2 \times 10^6$ IU/m$^2$.

Embodiment 4. The method of any one of embodiments 1 to 3, wherein the low dose IL-2 is administered once per day.

Embodiment 5. The method of any one of embodiments 1 to 3, wherein the low dose IL-2 is administered twice per week.

Embodiment 6. The method of any one of embodiments 1 to 3, wherein the low dose IL-2 is administered once per week.

Embodiment 7. The method of any one of embodiments 1 to 6, wherein the combination of the NAE inhibitor and low dose IL-2 provides an effect that is greater than the sum of either drug administered as a single agent.

Embodiment 8. The method of any one of embodiments 1 to 7, wherein the NAE inhibitor is:

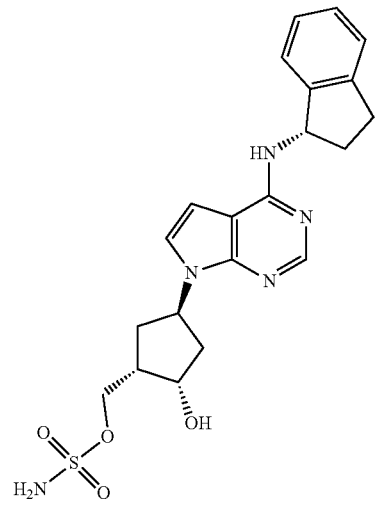

,

35
-continued
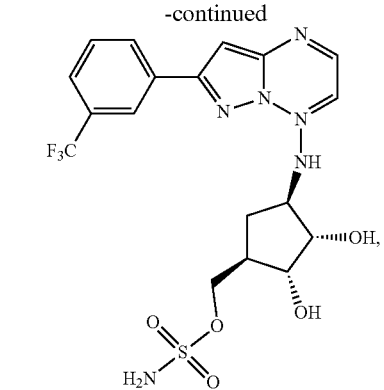
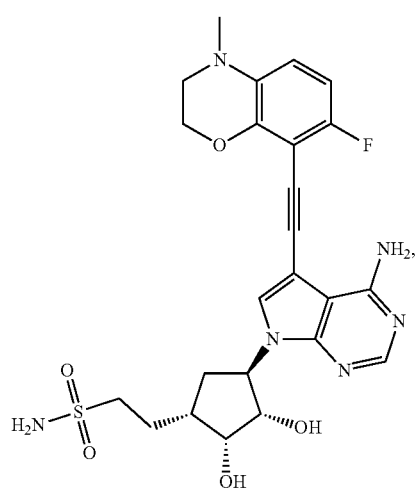
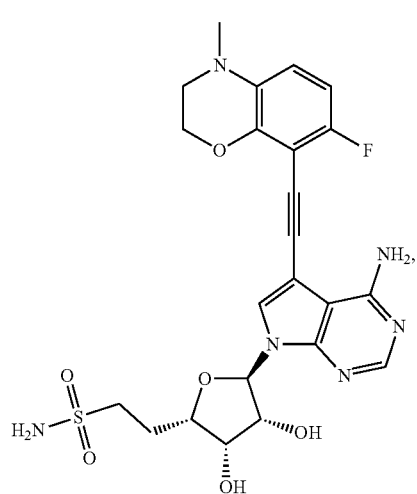
36
-continued
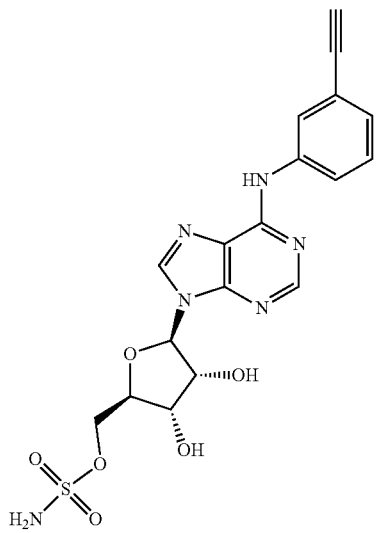
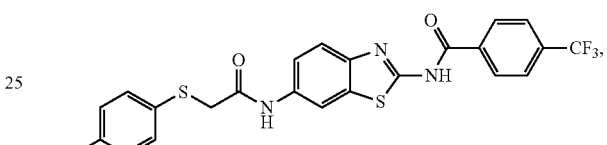
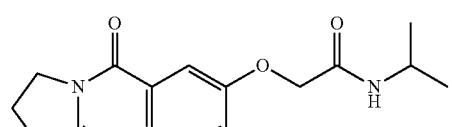
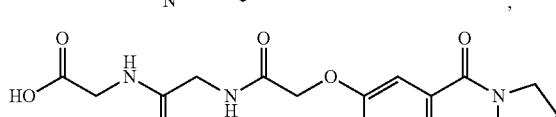
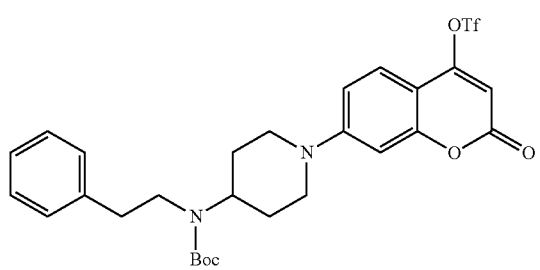
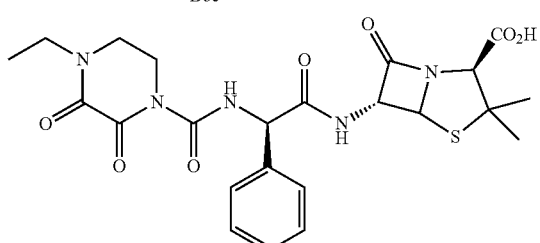
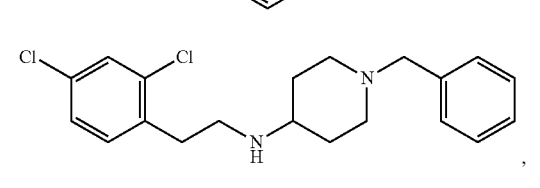

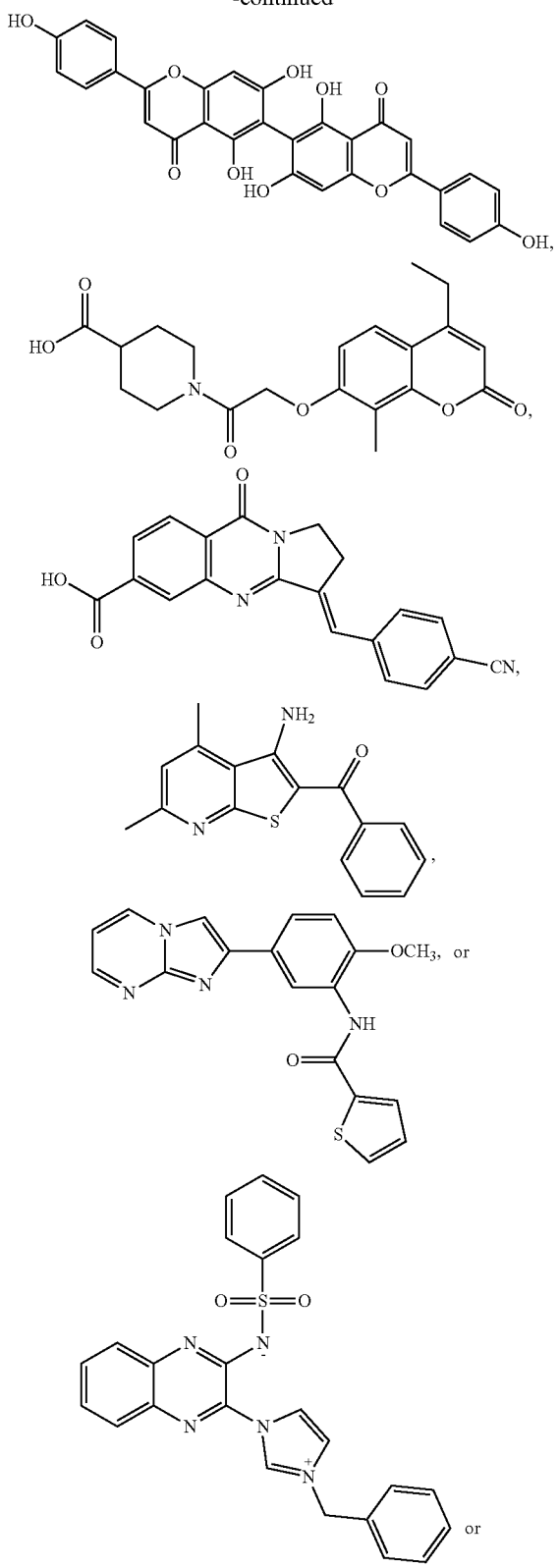

a pharmaceutically acceptable salt of any of the foregoing.

Embodiment 9. The method of any one of embodiments 1 to 8, wherein the NAE inhibitor is administered at a dose between about 1 mg/m2 to about 1000 mg/m2.

Embodiment 10. The method of any one of embodiments 1 to 9, wherein the NAE inhibitor is administered once per day.

Embodiment 11. The method of any one of embodiments 1 to 10, wherein the NAE inhibitor is administered once per week or twice per week.

Embodiment 12. The method of any one of embodiments 1 to 11, wherein the subject is human.

Embodiment 13. The method of any one of embodiments 1 to 12, wherein the inflammatory disorder is multiple sclerosis.

Embodiment 14. The method of any one of embodiments 1 to 12, wherein the inflammatory disorder is systemic lupus erythematosus.

Embodiment 15. The method of any one of embodiments 1 to 12, wherein the inflammatory disorder is type one diabetes (insulin-dependent diabetes mellitus).

Embodiment 16. A pharmaceutical composition comprising an effective dose of an NAE inhibitor; and an effective low dose of IL-2, for use in the method of any one of embodiments 1-15.

Embodiment 17. A kit for use in treating an inflammatory disorder in a subject in need thereof, comprising an effective dose of an NAE inhibitor; an effective low dose of IL-2; and instructions for use.

Embodiment 18. The pharmaceutical composition of embodiment 16, or the kit for use of embodiment 17, wherein the NAE inhibitor is:

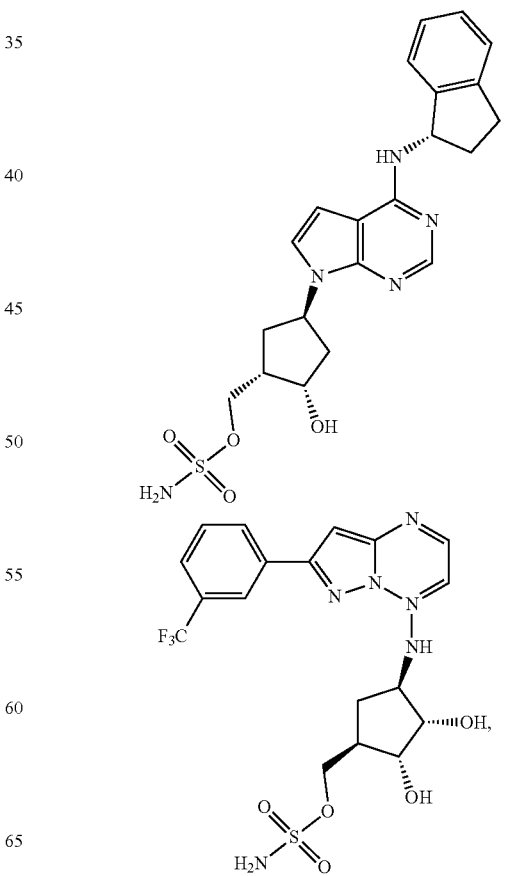

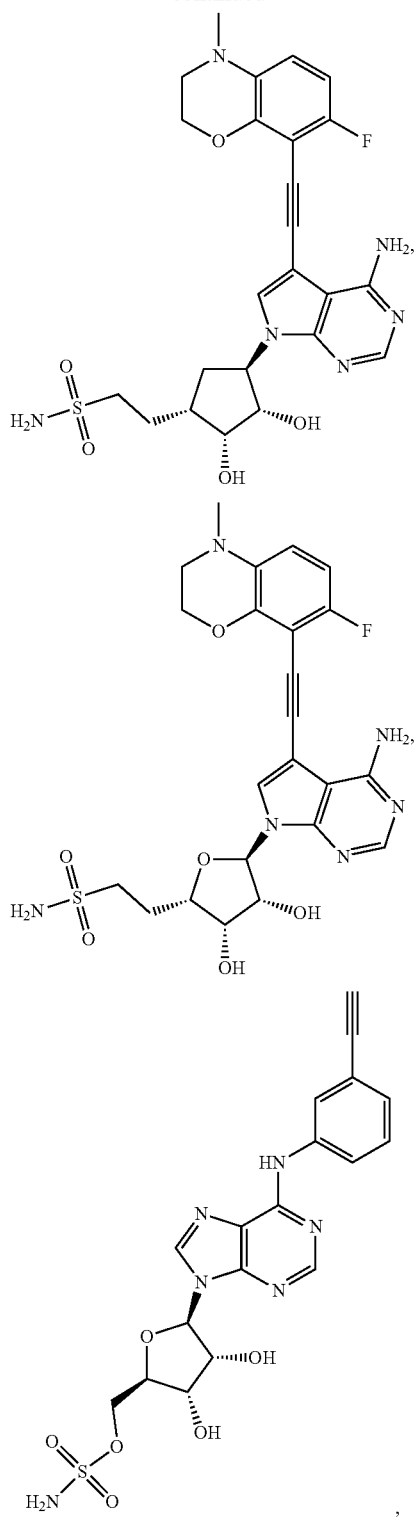
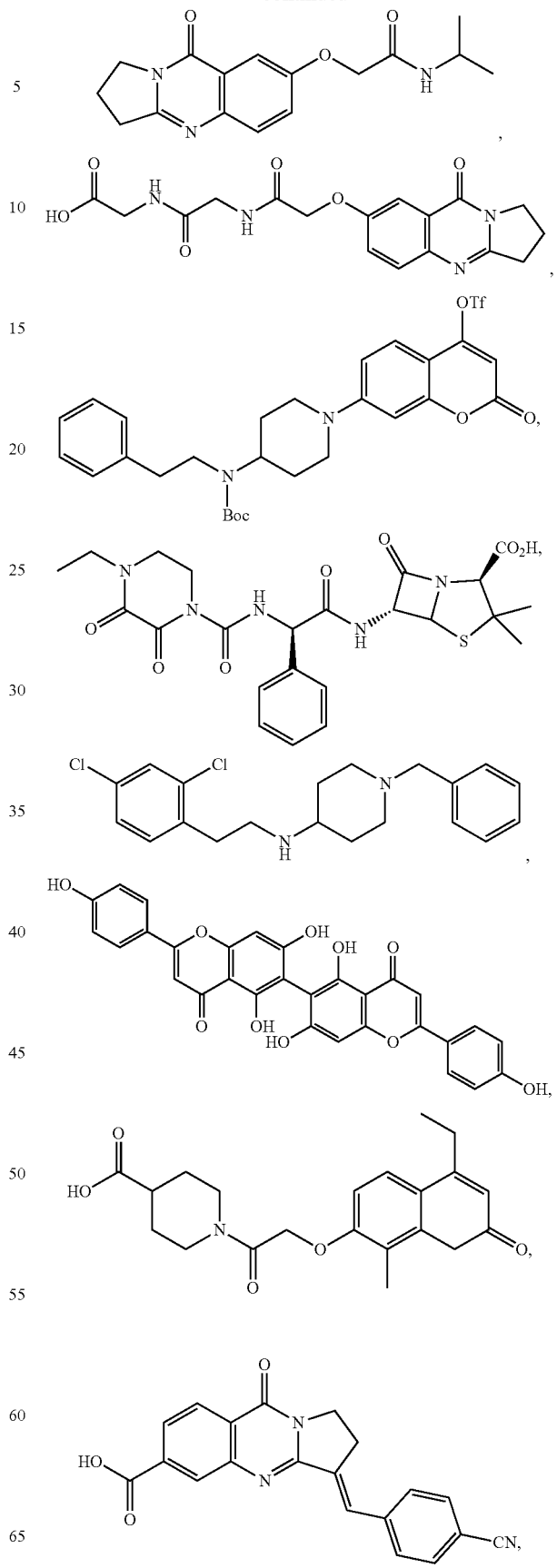

41

-continued

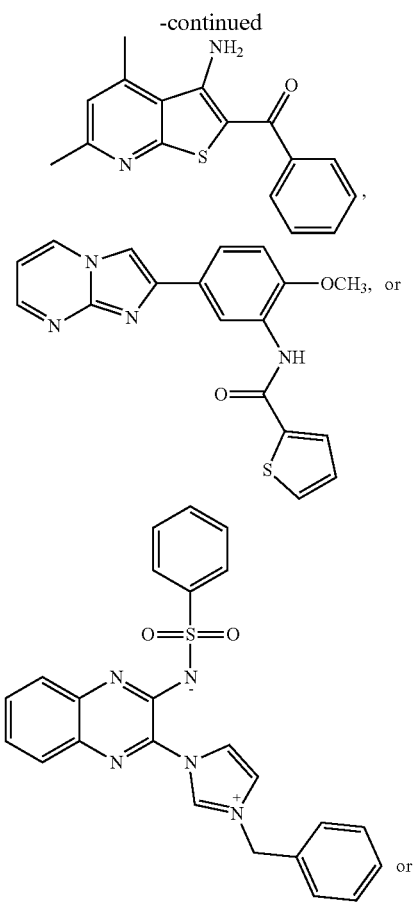

a pharmaceutically acceptable salt of any of the foregoing.

What is claimed is:

1. A method for treating systemic lupus erythematosus (SLE) in a subject in need thereof, comprising;
administering concomitantly to the subject:
(i) an effective dose of NEDD8 activating enzyme (NAE) inhibitor

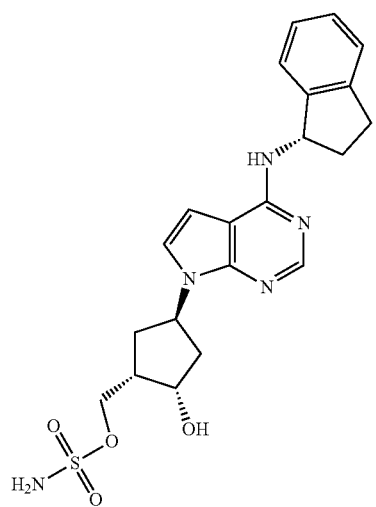

42 and
(ii) a low dose of IL-2 of from $0.05 \times 10^6$ IU/m$^2$ to $5 \times 10^6$ IU/m$^2$;
thereby increasing or restoring function of regulatory T lymphocytes (Tregs); and treating the SLE.

2. The method of claim 1, wherein the low dose of IL-2 is from about $0.1 \times 10^6$ IU/m$^2$ to about $2 \times 10^6$ IU/m$^2$.

3. The method of claim 1, wherein the low dose IL-2 is administered once per day.

4. The method of claim 1, wherein the low dose IL-2 is administered twice per week.

5. The method of claim 1, wherein the low dose IL-2 is administered once per week.

6. The method of claim 1, wherein the NAE inhibitor is administered at a dose between about 1 mg/m$^2$ to about 1000 mg/m$^2$.

7. The method of claim 1, wherein the NAE inhibitor is administered once per day.

8. The method of claim 1, wherein the NAE inhibitor is administered once per week or twice per week.

9. The method of claim 1, wherein the subject is human.

10. A method for treating systemic lupus erythematosus (SLE) in a subject in need thereof, comprising administering to the subject:
(i) an effective dose of an NEDD8 activating enzyme (NAE) inhibitor selected from:

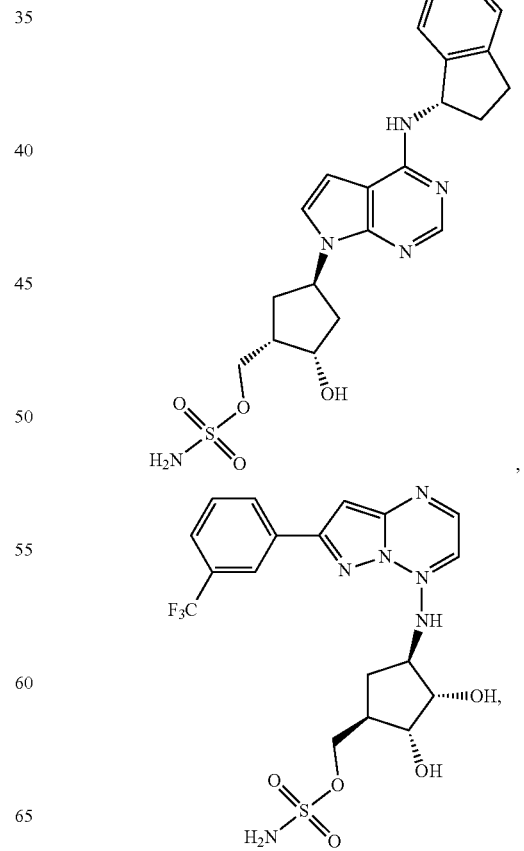

-continued
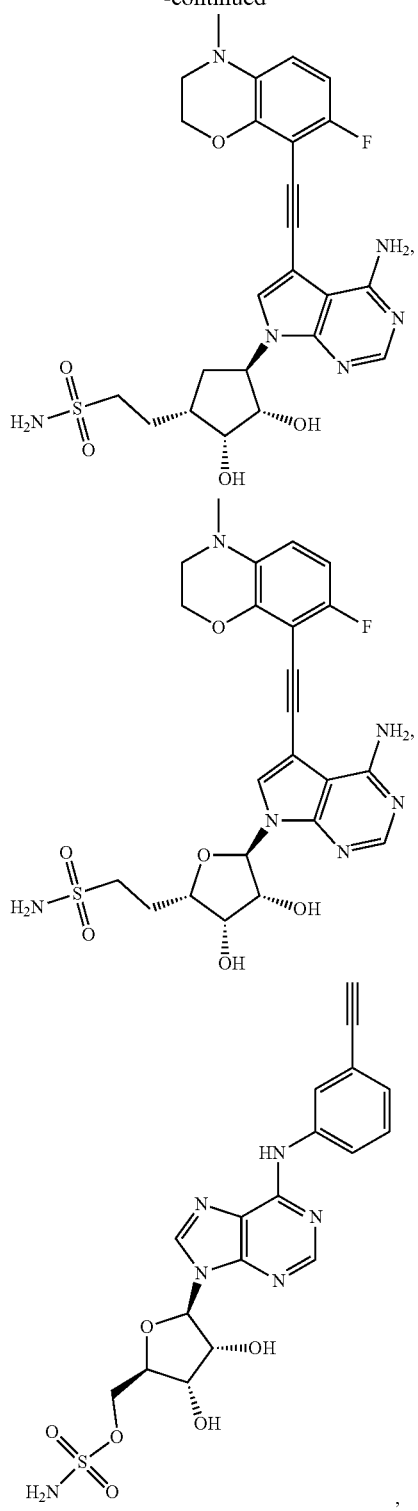
-continued
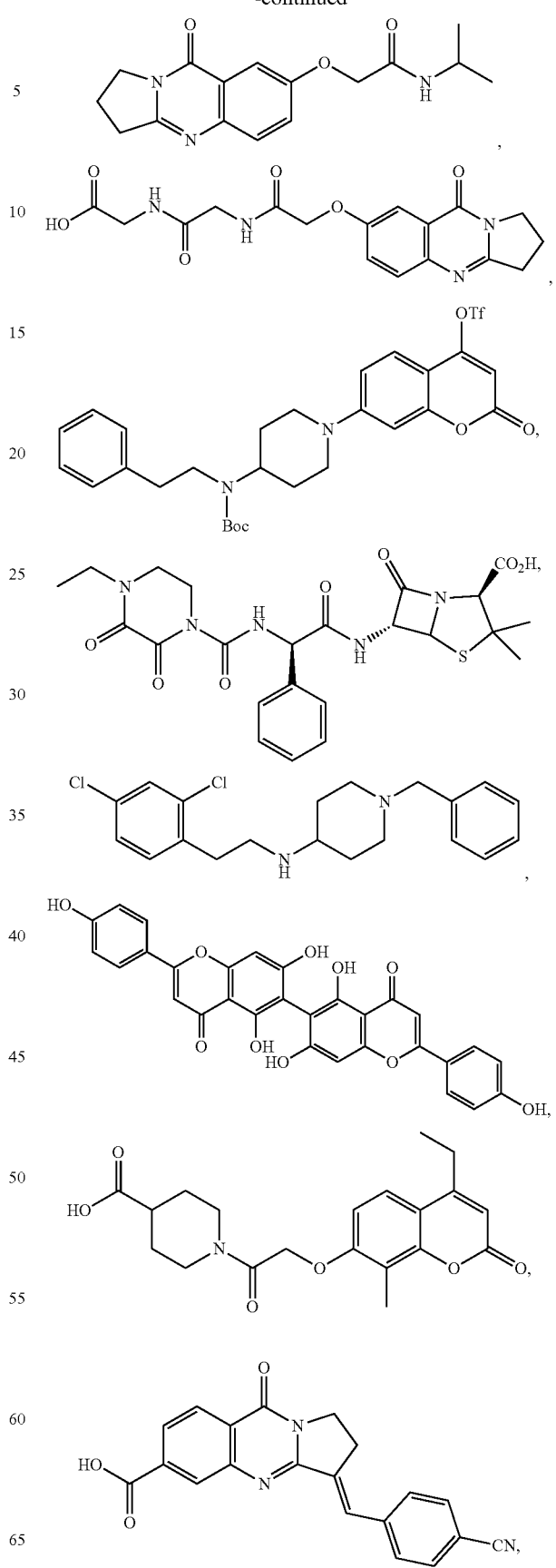

-continued

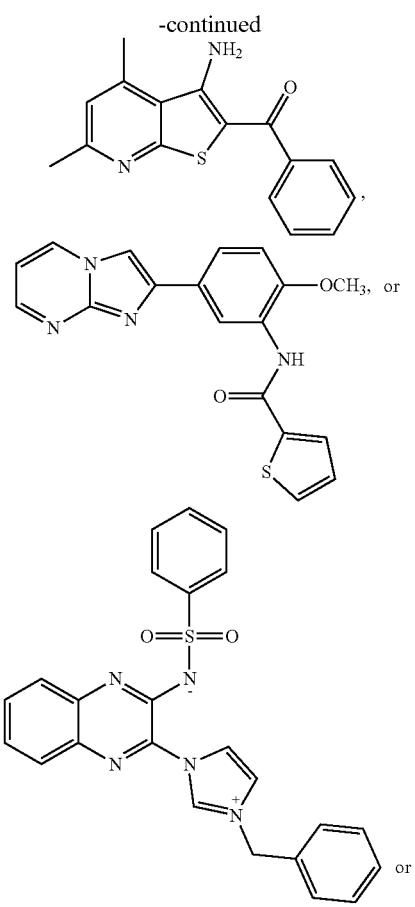

a pharmaceutically acceptable salt of any of the foregoing; and (ii) a low dose of IL-2 of from 0.05×10⁶ IU/m² to 5×10⁶ IU/m²;

thereby increasing or restoring function of regulatory T lymphocytes (Tregs) and treating the SLE.

11. A method for treating an inflammatory disease in a subject in need thereof, comprising administering to the subject:

(i) an effective dose of NEDD8 activating enzyme (NAE) inhibitor

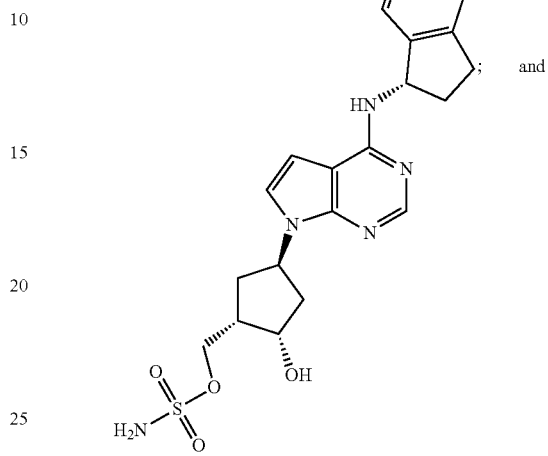

and (ii) a low dose of IL-2 of from $0.05 \times 10^6$ IU/m² to $5 \times 10^6$ IU/m²;

thereby increasing or restoring function of regulatory T lymphocytes (Tregs) and treating the inflammatory disease.

12. The method of claim 11, wherein the inflammatory disorder is multiple sclerosis.

13. The method of claim 11, wherein the inflammatory disorder is systemic lupus erythematosus.

14. The method of claim 11, wherein the inflammatory disorder is insulin-dependent diabetes mellitus.

* * * * *